US005885569A

United States Patent [19]
Windass

[11] Patent Number: 5,885,569

[45] Date of Patent: Mar. 23, 1999

[54] BIOLOGICAL INSECT CONTROL AGENT

[75] Inventor: John David Windass, Finchampstead, United Kingdom

[73] Assignee: Zeneca Limited, London, United Kingdom

[21] Appl. No.: 716,308

[22] PCT Filed: Mar. 27, 1995

[86] PCT No.: PCT/GB95/00677

§ 371 Date: Sep. 24, 1996

§ 102(e) Date: Sep. 24, 1996

[87] PCT Pub. No.: WO95/26410

PCT Pub. Date: Oct. 5, 1995

[30] Foreign Application Priority Data

Mar. 25, 1994 [GB] United Kingdom .................. 9405951

[51] Int. Cl.$^6$ ............................ A01N 63/00; C12N 7/00; C12N 7/01; C12N 15/79

[52] U.S. Cl. ....................... 924/93.2; 424/93.6; 435/69.1; 435/235.1; 435/320.1

[58] Field of Search ............................... 435/235.1, 69.1, 435/71.1, 70.1, 320.1; 424/93.1, 73.2, 93.6

[56] References Cited

FOREIGN PATENT DOCUMENTS

| | | |
|---|---|---|
| 0 505 207 | 9/1992 | European Pat. Off. . |
| 0 556 160 | 8/1993 | European Pat. Off. . |
| 88/07087 | 9/1988 | WIPO . |
| 90/10387 | 9/1990 | WIPO . |
| 92/06181 | 4/1992 | WIPO . |
| 93/18145 | 9/1993 | WIPO . |
| 93/22442 | 11/1993 | WIPO . |
| 94/00585 | 1/1994 | WIPO . |
| 94/23047 | 10/1994 | WIPO . |
| 95/14084 | 5/1995 | WIPO . |

OTHER PUBLICATIONS

Ashburner, M., et al., *Developmental Genetics,* "On the Evolutionary Relationships of *Drosophilia melanogaster,*" 1984, vol. 4, pp. 295–312.

Bonning, B. C., *Journal of General Virology,* "Superior expression of juvenile hormone esterase and β–galactosidase from the basic protein promoter of *Autographa californica* nuclear polyhedrosis virus compared to the p10 protein and polyhedrin promotors," 1994, vol. 75, pp. 1551–1556.

Cammue, B.P.A., et al., *The Journal of Biological Chemistry,* "Isolation and Characterization of a Novel Class of Plant Antimicrobial Peptides from *Mirabilis jalapa* L. Seeds," 1992, vol. 267(4), pp. 2228–2233.

Eldridge, R., et al., *Journal of Virology,* "Characterization of a Baculovirus Gene Encoding a Small Conotoxinlike Polypeptide," 1992, vol. 66(11), pp. 6563–6571.

Fainzilber, M., et al., *Eur. J. Biochem.,* "Mollusc–specific toxins from the venom of Conus textile neovicarius," 1991, vol. 202, pp. 589–595.

Hillyard, D.R., et al., *Biochemistry,* "A Molluscivorous Conus Toxin: Conserved Frameworks in Conotoxins," 1989, vol. 28, pp. 358–361.

Hughes, P.R., et al., *Journal of Invertebrate Pathology,* "A Synchronoous Peroral Technique for the Bioassay of Insect Viruses," 1981, vol. 37, pp. 154–159.

Ikemura, T., *Mol. Biol. Evol.,* "Codon Usage and tRNA Content in Unicellular and Multicellular Organisms," 1985, vol. 2(1), pp. 13–34.

Kozak, M., *J. Mol. Biol.,* "At Least Six Nucleotides Preceding the AUG Initiator Codon Enhance Translation in Mammalian Cells," 1987, vol. 196, pp. 947–950.

Kozak, M., *Cell,* "Point Mutations Define a Sequence Flanking the AUG Intiatator Codon That Modulates Translation by Eukaryotic Ribosomes," 1986, vol. 44, pp. 283–292.

Kozak, M., *Nucleic Acids Research,* "Compilation and analysis of sequences upstream from the translational start site in eukaryotic Mrnas," 1984, vol. 12(2), pp. 857–872.

Kozak, M., *Nucleic Acids Research,* "Possible role of flanking nucleotides in recognition of the AUG initiator codon by eukaryotic ribosomes," 1981, vol. 19(20), pp. 5233–5252.

McCutchen, B.F., *Bio/Technology,* "Development of a Recombinant Baculovirus Expressing an Insect–Selective Neurotoxin: Potential for Pest Control," 1991, vol. 9, pp. 848–852.

Miller, D. W., *Biotechnology for Crop Protection,* "Genetically Engineered Viral Insecticides," 1988, pp. 405–421.

Olivera, B. M., et al., *Science,* "Diversity of Conus Neuropeptides," 1990, vol. 249, pp. 257–263.

Olivera, B. M., et al., *Journal of Biological Chemistry,* "Conotoxins", 1991, vol. 266(33), pp. 22067–22070.

Possee, R.D., et al., *Nucleic Acids Research,* "Analysis of the polyhedrin gene promoter of the *Autographa californica* nuclear polyhedrosis virus," 1987, vol. 15(24), pp. 10233–10248.

Sharp, P. M., et al., *Nucleic Acids Research,* "Codon usage in yeast: cluster analysis clearly differentiates highly and lowly expressed genes," 1986, vol. 14(13), pp. 5125–5143.

Stewart, L.M.D, et al., *Nature,* "Construction of an improved baculovirus insecticide containing an insect–specific toxin gene," 1991, vol. 352, pp. 85–88.

Tomalski, M.D., et al., *Bio/Technology,* "Expression of a Paralytic Neurotoxin Gene to Improve Insect Baculoviruses as Biopesticides," 1992, vol. 10, pp. 545–549.

(List continued on next page.)

*Primary Examiner*—Nancy Degen
*Attorney, Agent, or Firm*—Marian T. Thomson

[57] ABSTRACT

A recombinant baculovirus for use as an insect control agent having a genome which comprises a polyhedrin gene and a heterologous gene, which expresses an insecticidal protein, wherein the polyhedrin gene and the heterologous gene are not under the control of the same promoter, and are located on the genome such that viral progeny produced by a recombination event with wild-type baculovirus which are viable do not retain expression of both the polyhedrin gene and the heterologous gene.

13 Claims, 16 Drawing Sheets

OTHER PUBLICATIONS

Tomalski, M.D., et al., *Nature,* "Insect paralysis of baculovirus–mediated expression of a mite neurotoxin gene," 1991, vol. 352, pp. 82–85.

von Heijne, G., *Nucleic Acids Research,* "A new method for predicting signal sequence cleavage sites," 1986, vol. 14(11), pp. 4683–4691.

Wada, K., et al., *Nucleic Acids Research,* "Codon usage tabulated from the GenBank genetic sequence data," 1991 vol. 20, Supplement, pp. 2111–2118.

Weyer, U., et al., *Journal of General Virology,* "Analysis of very late gene expression by *Autographa californica* nuclear polyhedrosis virus and the further development of multiple expression vectors," 1990, vol. 71, pp. 1525–1534.

Wood, H. A., et al., *Annu. Rev. Microbiol.,* "Genetically Engineered Baculoviruses as Agents for Pest Control," 1991, vol. 45, pp. 69–87.

Woodward, S.R., *The EMBO Journal,* "Constant and hypervariable regions in conotoxin propeptides," 1980, vol. 9(4), pp. 1015–1010.

Sambrook, J. et al., *Molecular Cloning—A Laboratory Manual,* 2d Ed., pp. 1.63–1.67, 1.90–1.91, A.10 and 1.74–1.75, 1989.

Arif, B.M., *Current Topics in Microbiology and Immunology,* "The Structure of the Viral Genome," 1986, vol. 131, pp. 21–29.

King, L.A., et al., *The Baculovirus Expression System,* "The Development of Baculovirus Expression Vectors," 1992, pp. 17–29 and 135–140.

Spurr, A. R., *J. Ultrastructure Research,* "A Low–Viscosity Epoxy Resin Embedding Medium for Electron Microscopy," 1969, vol. 26, pp. 31–43.

Pang et al. "Synthesis & Toxicity of Full Length & Truncated Bacterial CryIVD Mosquitocidal Proteins" J. Gen Virl 73 89–101, 1992.

| FIG. 6A |
|---|
| FIG. 6B |

COMPARATIVE STRUCTURAL FEATURES OF THE GENOMES OF RECOMPINANT BACULOVIRUSES AcMNPV/pAcUW21/sKK-O #1 AND AcUW1-PH/sKK-O #2

Sequence of a Synthetic KK-0 Conotoxin (sKK-0) Gene
Showing the Region.Encoding Pre-Pro Conotoxin KK-0

```
        10         20         30         40         50         60

                 MetL ysLeuThrCy sMetHetIle ValAlaValL euPheLeuTh
TTAGATCTAA TTCACCATGA AGCTGACATG TATGATGATC GTGGCCGTGC TGTTCCTGAC
AATCTAGATT AAGTGGTACT TCGACTGTAC ATACTACTAG CACCGGCACG ACAAGGACTG

        70         80         90        100        110        120

rAlaTrpThr PheAlaThrA laAspAspPr oArgAsnG]y LeuGlyAsnL euPheSerAs
CGCCTGGACC TTCGCCACTG CAGACGATCC CCGCAACGGC CTGGGCAACC TGTTCTCCAA
GCGGACCTGG AAGCGGTGAC GTCTGCTAGG GGCGTTGCCG GACCCGTTGG ACAAGAGGTT
-----------------------------------------------------------------
```

FIG. 7A

```
       130        140        150        160        170        180
                                                    *
nAlaHisHis GluHetLysA snProGluAl aSerLysLeu AsnLysArgT rpCysLysGl
CGCCCACCAC GAAATGAAGA ACCCCGAGGC ATCCAAGCTT AACAAGCGCT GGTGTAAGCA
GCGGGTGGTG CTTTACTTCT TGGGGCTCCG TAGGTTCGAA TTGTTCGCGA CCACATTCGT

       190        200        210        220        230        240

nSerG]yGlu MetCysAsnL euLeuAspGl nAsnCysCys AspGlyTyrC ysIIeVa]Le
GTCCGGAGAG ATGTGTAACC TGCTGGACCA GAACTGTTGT GACGGCTACT GTATCGTGCT
CAGGCCTCTC TACACATTGG ACGACCTGGT CTTGACAACA CTGCCGATGA CATAGCACGA

       250        260        269

uValCysThr ---
GGTGTGCACC TAGTGACGGC CGGATCCTT
CCACACGTGG ATCACTGCCG GCCTAGGAA
```

The arrow (*) indicates the presumed processing site used to release mature conotoxin KK-0 from it's precursor.

FIG. 7B

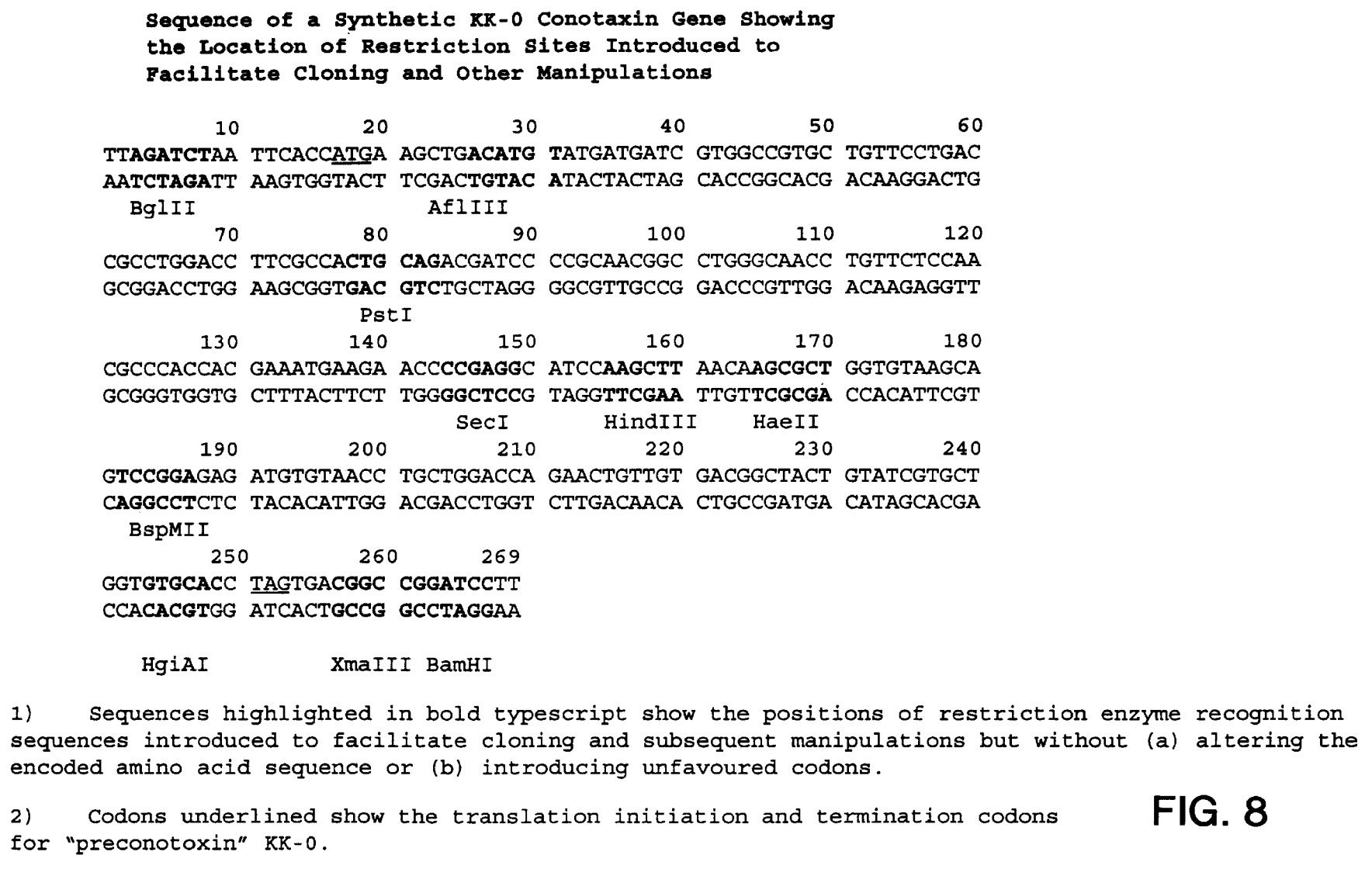

Sequence of a Synthetic KK-0 Conotaxin Gene Showing the Location of Restriction Sites Introduced to Facilitate Cloning and Other Manipulations

10 20 30 40 50 60
TTAGATCTAA TTCACC<u>ATG</u>A AGCTGACATG TATGATGATC GTGGCCGTGC TGTTCCTGAC
AATCTAGATT AAGTGGTACT TCGACTGTAC ATACTACTAG CACCGGCACG ACAAGGACTG
BglII AflIII 70 80 90 100 110 120
CGCCTGGACC TTCGCCACTG CAGACGATCC CCGCAACGGC CTGGGCAACC TGTTCTCCAA
GCGGACCTGG AAGCGGTGAC GTCTGCTAGG GGCGTTGCCG GACCCGTTGG ACAAGAGGTT
PstI 130 140 150 160 170 180
CGCCCACCAC GAAATGAAGA ACCCCGAGGC ATCCAAGCTT AACAAGCGCT GGTGTAAGCA
GCGGGTGGTG CTTTACTTCT TGGGGCTCCG TAGGTTCGAA TTGTTCGCGA CCACATTCGT
SecI HindIII HaeII 190 200 210 220 230 240
GTCCGGAGAG ATGTGTAACC TGCTGGACCA GAACTGTTGT GACGGCTACT GTATCGTGCT
CAGGCCTCTC TACACATTGG ACGACCTGGT CTTGACAACA CTGCCGATGA CATAGCACGA
BspMII 250 260 269
GGTGTGCACC <u>TAG</u>TGACGGC CGGATCCTT
CCACACGTGG ATCACTGCCG GCCTAGGAA HgiAI XmaIII BamHI 1) Sequences highlighted in bold typescript show the positions of restriction enzyme recognition sequences introduced to facilitate cloning and subsequent manipulations but without (a) altering the encoded amino acid sequence or (b) introducing unfavoured codons.

2) Codons underlined show the translation initiation and termination codons for "preconotoxin" KK-0.

FIG. 8

Sequence and Relationships of Oligonucleotides Used For the Assembly of a Synthetic KK-O Conotoxin Gene sKK-0

```
                 10         20         30         40         50         60

  ConoA
  5'-TTAGATCTAA TTCACCATGA AGCTGACATG TATGATGATC GTGGCCGTGC TGTTCCTGAC
  5'-TTAGATCTAA TTCACCATGA AGCTGACATG
    ConoPCR1

                 70         80         90        100        110        120

     CGCCTGGACC TTCGCCACTG CAGA
          CCTGG AAGCGGTGAC GTCTGCTAGG GGCGTTGCCG GACCCGTTGG ACAAGAGGTT
          ConoB

                130        140        150        160        170        180

           ConoC
        5'-CAC GAAATGAAGA ACCCCGAGGC ATCCAAGCTT AACAAGCGCT GGTGTAAGCA
     GCGGGTGGTG CTTTACTTCT TGGGGCTCCG GTAGG-5'

                190        200        210        220        230        240

     GTCCGGAGAG ATGTGTAACC TGCTGGACCA GAACTG
                     CATTGG ACGACCTGGT CTTGACAACA CTGCCGATGA CATAGCACGA
                    ConoD
                250        260        269
                                ConoPCR2
        CACGTGG ATCACTGCCG GCCTAGGAA-5'
     CCACACGTGG ATCACTGCCG GCCTAGGAA-5'
```

FIG. 9

Sequence Determined for the sKK-0 Insert Region of Transfer Vector pVL1392/sKK-0 #2.2

===02-MAR-1994=====================================================PC/GENE=

SEQUENCE OF PVL1392 / SYNTHETIC CONOTOXIN GENE READ WITH SEQUENCING
OLIGO pVL1392REV (27/3/92) CLONE 2.2

| | 10 | 20 | 30 | 40 | 50 | 60 |
|---|---|---|---|---|---|---|
| 1 | GGCGCGGATC | **AGATCTAATT** | **CACCATGAAG** | **CTGACATGTA** | **TGATGATCGT** | **GGCCGTGCTG** |
| 61 | **TTCCTGACCG** | **CCTGGACCTT** | **CGCCACTGCA** | **GACGATCCCC** | **GCAACGGCCT** | **GGGCAACCTG** |
| 121 | **TTCTCCAACG** | **CCCACCACGA** | **AATGAAGAAC** | **CCCGAGGCAT** | **CCAAGCTTAA** | **CAAGCGCTGG** |
| 181 | **TGTAAGCAGT** | **CCGGAGAGAT** | **GTGTAACCTG** | **CTGGACCAGA** | **ACTGTTGTGA** | **CGGCTACTGT** |
| 241 | **ATCGTGCTGG** | **TGTGCACCTA** | **GTGACGGCCG** | CTCCAGAATT | CT | |

Total number of bases is: 282.
DNA sequence composition: 64 A; 83 C; 76 G; 59 T; 0 OTHER;

Sequence name: CON022REV

===02-MAR-1994=====================================================PC/GENE=

Sequence tract emboldened corresponds to that anticipated from the design of gene sKK-0.

Flanking sequences shown in normal script correspond to the sequence of the appropriate region of pVL1392 (data from InVitrogen Corp., 3985 Sorrento Valley Boulevard, San Diego, California).

FIG. 11

Comparisons of the Predicted Amino Acid Sequences of (A) the Precursors of Conus textile KK-0, KK-1 and KK-2 Peptides and (B) Predicted Sequences of the Corresponding Nature Peptides. (Taken from Woodward et al, (1990) EMBO J. 9 1015-1020).

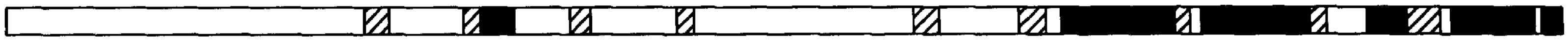

```
KK-0 ···MKLTCMMIVAVLFLTAWTFATADDPANGLGNLFSNAHHEMKHPEASKLNKRWCKQSGEMCNLLDQNCCDGYCIVIVCT
KK-1                           SG   E    K                  - IEQFDP  EMIRHT   V V FLMA I
KK-2                      V    SG   E    K              N   - APFLHP  TFFFP    HSV CQFI L
```

ALL THREE DIFFERENT
Two identical
All three identical

FIG. 12A

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| KK-0 | W | C | K | Q | S | G | E | M | C | N | L | L | D | Q | N | C | C | D | G | Y | C | I | V | L | V | C | T |
| KK-1 | | C | I | E | Q | F | D | P | C | E | M | I | R | H | T | C | C | V | G | V | C | F | L | M | A | C | I |
| KK-2 | | C | A | P | F | L | H | P | C | T | F | F | F | P | N | C | C | N | S | Y | C | V | Q | F | I | C | L |
| ωMVIIA | | C | K | G | K | G | A | K | C | S | R | L | M | Y | D | C | C | T | G | S | C | R | S | G | K | C | |

FIG. 12B

BIOLOGICAL INSECT CONTROL AGENT

The present invention relates to a baculovirus for use as an insect biological control agent, and more particularly to a baculovirus comprising a heterologous gene capable of expressing an insecticidal protein, use of the baculovirus to minimise production of certain viral progeny, and a method of controlling insect pests.

By insect biological control agent we mean an agent which when brought into association with an insect is capable of infecting the insect and interfering with the normal biochemical and physiological processes and leading ultimately to the disablement or death of the insect.

Baculoviruses constitute one of the largest and most diverse groups of insect-pathogenic viruses, and are commonly used as powerful expression systems for heterologous proteins. There is now great interest in baculoviruses as insect biological control agents. In particular, work is being carried out on improving the time the virus takes to kill its host insect by combining the pathogenicity of the baculovirus with the insecticidal action of a toxin, hormone, or enzyme which is active on insects.

A concern over the use of recombinant baculoviruses capable of expressing a heterologous insecticidal gene product to produce enhanced and commercially viable levels of insecticidal activity is that the recombinant baculoviruses might compete with wild-type viruses and hence become established within the environment, even perhaps taking over from the wild-type virus populations. By wild-type baculovirus, we mean a non-recombinant baculovirus. Emphathis is therefore being put on developing recombinant baculoviruses which do not need to persist in the environment to deliver an insecticidal effect.

With the objective of reducing the survival capacity of the recombinant baculoviruses used as insecticides various, more-or-less, complex systems have been proposed. Each of these proposals has potential drawbacks.

For example, Miller at al (Biotechnology for Crop Protection, 1988, Ed. Hedin et al, pp 405) proposed that effective, safe recombinant baculoviruses could be produced by a co-occlusion method. In this method recombinant baculoviruses, which themselves lack the capacity to express the polyhedrin gene necessary for the production of the occlusion bodies required to provide environmental stability, are propagated in mixed infections with wild-type viruses, which provide the polyhedrin protein. Polyhedra containing both recombinant and wild-type virus particles are produced. The idea behind this proposal was that the co-occlusion process would provide a method for delivering a polyhedrin minus ($pol^-$) baculovirus, i.e. lacks the functional polyhedrin gene, to the field in an infectious form. Persistence of the co-occluded $pol^-$ baculovirus in a virus population is determined by the probability of co-infection of individual larvae and cells with both virus types as the virus is passed from insect to insect.

Limited field trials of the survival characteristics of co-occluded virus populations have been reported by Wood et al (see the general review—Annu. Rev. Microbiol. (1991), 45, p69–87, in particular page 83). Perhaps rather surprisingly the rate of decline of the polyhedrin deficient genomes from the population of baculovirus was found to be slow.

From a production standpoint, preparation of co-occluded virus populations will also be technically demanding, requiring very carefully controlled dual infection methods, and essentially wasteful, as a significant proportion of the product is useless with respect to delivering an improved insecticidal effect.

An alternative approach to the use of genetic manipulation to provide baculovirus populations which are genetically deficient in the ability to make polyhedra is to replicate baculoviruses which lack the functional polyhedra gene in a cell line/host which has been genetically engineered to express the missing polyhedrin. In use the resultant virus particles are active per os, but after propagation the wild-type virus cannot produce polyhedrin or occlusion bodies. The progeny of such infections have very low stability and/or poor infective capacity.

Drawbacks with this approach are (i) that polyhedrin levels during natural baculovirus infections are very large at the time of occlusion body production, and reproducing such expression levels in cell lines will be very difficult, and (ii) that the cell line/host must carry the functional polyhedrin gene. There is thus a significant likelihood that the recombination events would result in the production of viral genomes which have retained the capacity to produce the insecticidal protein and acquired the capacity to make polyhedrin. Once released into the environment such baculoviruses will behave like a genetically engineered polyhedrin plus ($pol^+$) virus, i.e. contains the functional polyhedrin gene.

Wood et al (International Patent Publication No. 93/22442) suggest that supply of polyhedrin and the ability to produce occluded viruses is not always necessary to produce baculoviruses with a high level of per os activity. So-called "pre-occluded" viruses generated in the nucleus of cells infected with polyhedrin deficient viruses are reported to be orally active and are expected to have the limited survival properties of non-occluded viruses. However, realisation of this approach will be dependent upon the development of formulation techniques which can protect the "pre-occluded" virions for a sufficient period that there is a high probability of the target pest insect encountering and ingesting the virus in the field before it has been inactivated. In natural occlusion bodies polyhedrin fulfils this function, at least in part.

The genome of the baculovirus is a closed circular superhelical molecule of double-stranded DNA. Variations of the genome structure have been observed within a strain. The difference in DNA sequence may be as a result of reduplication of portions of the genome, deletions of sequences, and base substitutions. Reiterated DNA sequences have also been found within genomes, for example it is reported that the genome of AcMNPV possesses five regions which show DNA homology. There have been several reports of intergenic homology among baculoviruses. For example, the polyhedrin gene and a region encompassing the p10 gene are highly conserved among Nuclear Polyhedrosis Viruses (NPVs) infecting Lepidoptera.

There have also been reported cases of insertion of host cell DNA sequences into the viral genome. In particular, cellular DNA has also been reported to be incorporated into the genome of two closely related viruses, AcMNPV and *Galleria mellonella* NPV (GmMNPV). Without wishing to be bound by any theory it is believed that the homologous regions may be associated with such genome mutations. More recently, five regions which may be associated with insertion of cellular DNA into the genome of SeMNPV were identified. For a general review see Arif BM 'The Structure of the Viral Genome', pg 26–27, in 'Current Topics in Microbiology and Immunology'—The Molecular Biology of Baculoviruses', Ed. Doerfler and Bohm.

It was therefore realised that as well as competition with wild-type viruses, a problem with release of recombinant baculoviruses may be that they would interact with wild-types in homologous recombination events leading to novel baculoviruses. In such homologous recombination events a region of DNA occuring between two regions of the genome which are homologous with regions of a genome of a second virus are transferred, or swapped, between the viruses. Although any risks involved in the release of a recombinant baculovirus would have been assessed before release, the progeny of any such combinations with wild-types may well have altered insect host ranges and/or changed virulence for target pests.

According to one aspect of the present invention there is provided a recombinant baculovirus for use as an insect biological control agent having a genome which comprises a heterologous gene and a polyhedrin gene, which expresses an insecticidal protein, wherein the heterologous gene and the polyhedrin gene are not under the control of the same promoter and the heterologous gene and the polyhedrin gene are sufficiently spaced apart so as to minimise production of viable viral progeny of recombination events with wild-type baculovirus which retain expression of both the polyhedrin and heterologous gene.

According to another aspect of the present invention there is provided a recombinant baculovirus for use as an insect control agent having a genome which comprises a polyhedrin gene and a heterologous gene, which expresses an insecticidal protein, wherein the polyhedrin gene and the heterologous gene are not under the control of the same promoter, and are located on the genome such that viral progeny produced by a recombination event with wild-type baculovirus which are viable do not retain expression of both the polyhedrin gene and the heterologous gene.

By viable we mean that the progeny does not lack an essential gene.

The present invention can best be described with reference to the following accompanying drawings.

Figure 5A:
Figure 5B:
Figure 5C:
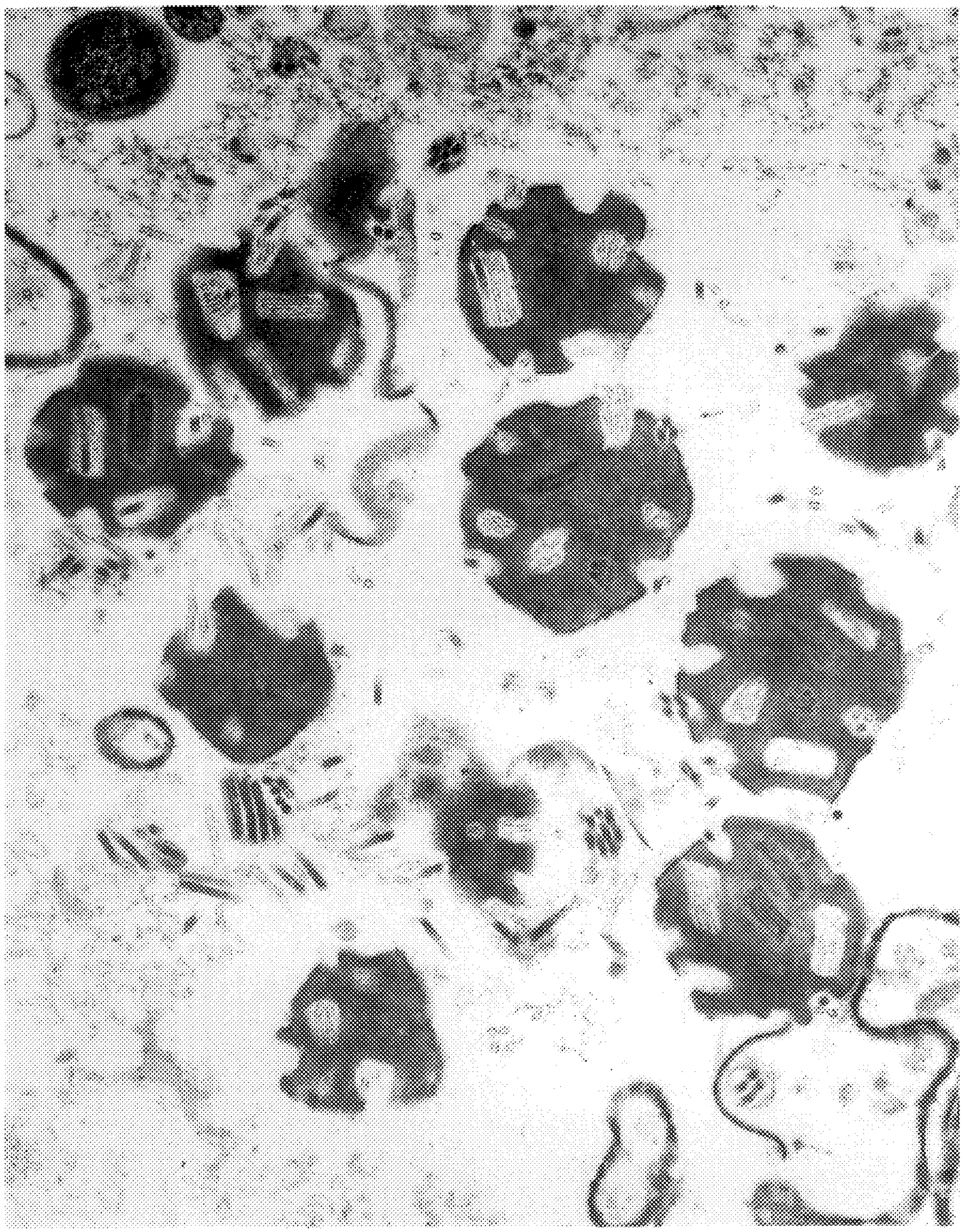
Figure 5D:
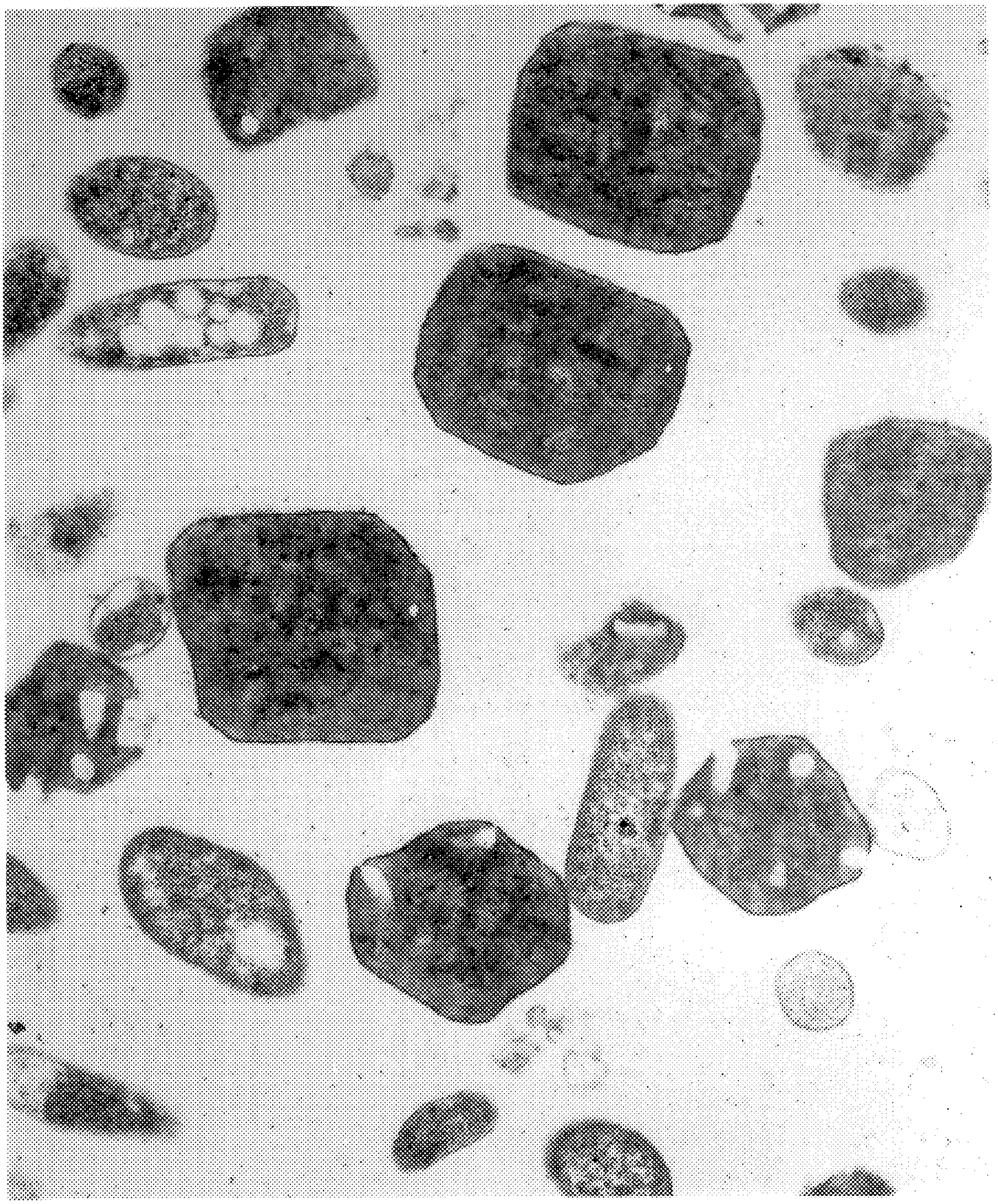
Figures 6, 6A:
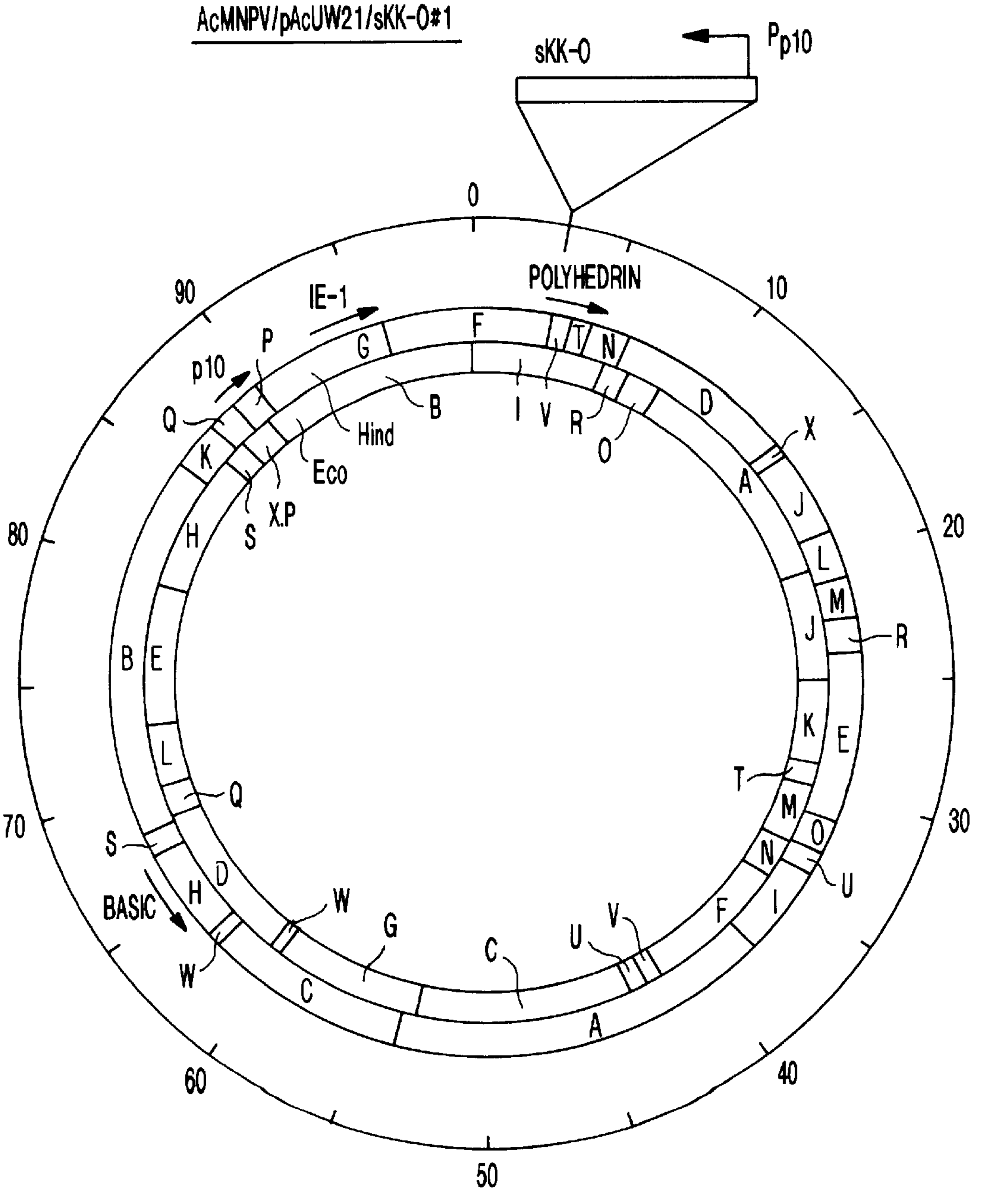
Figure 6B:
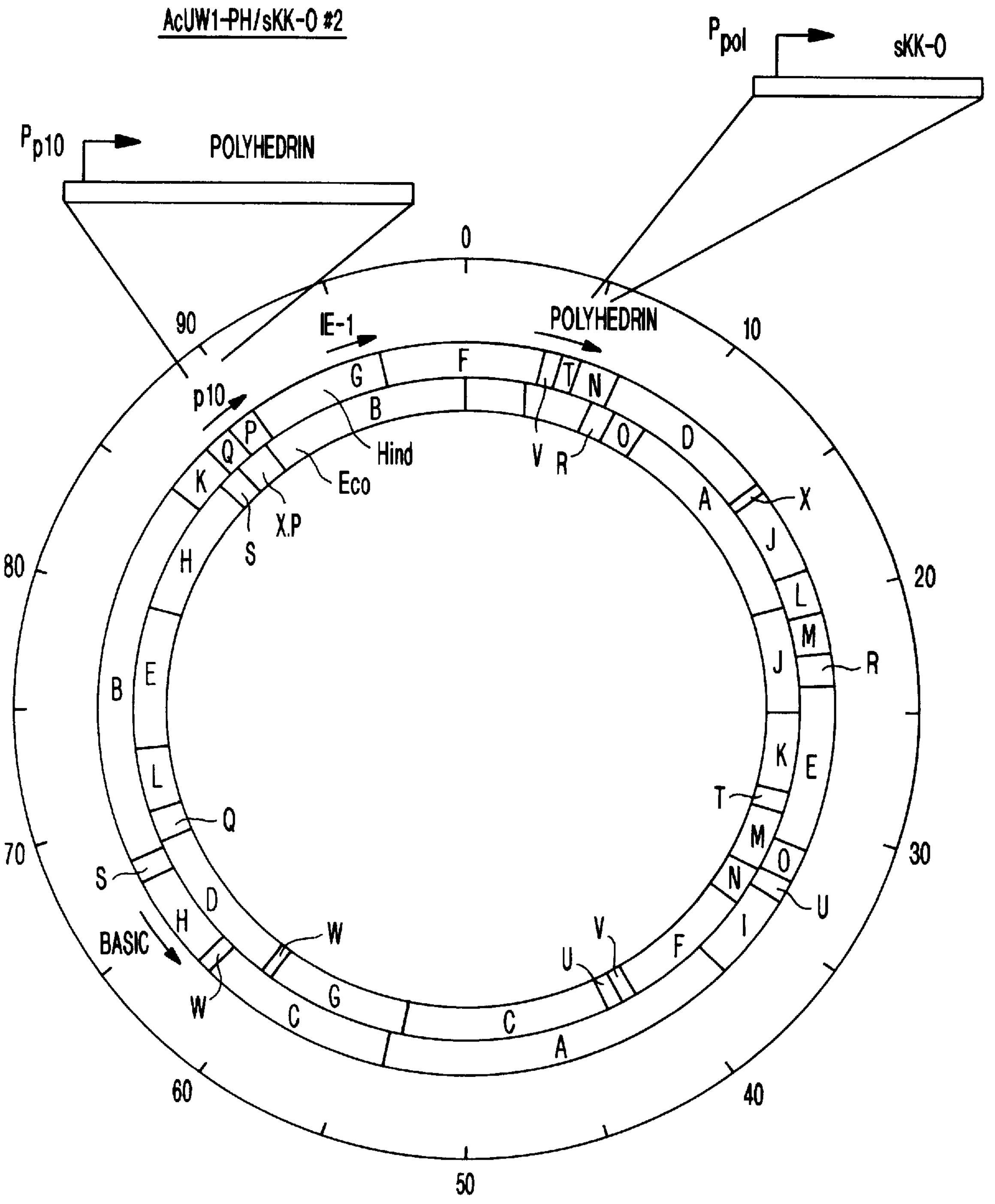
Figure 10A:
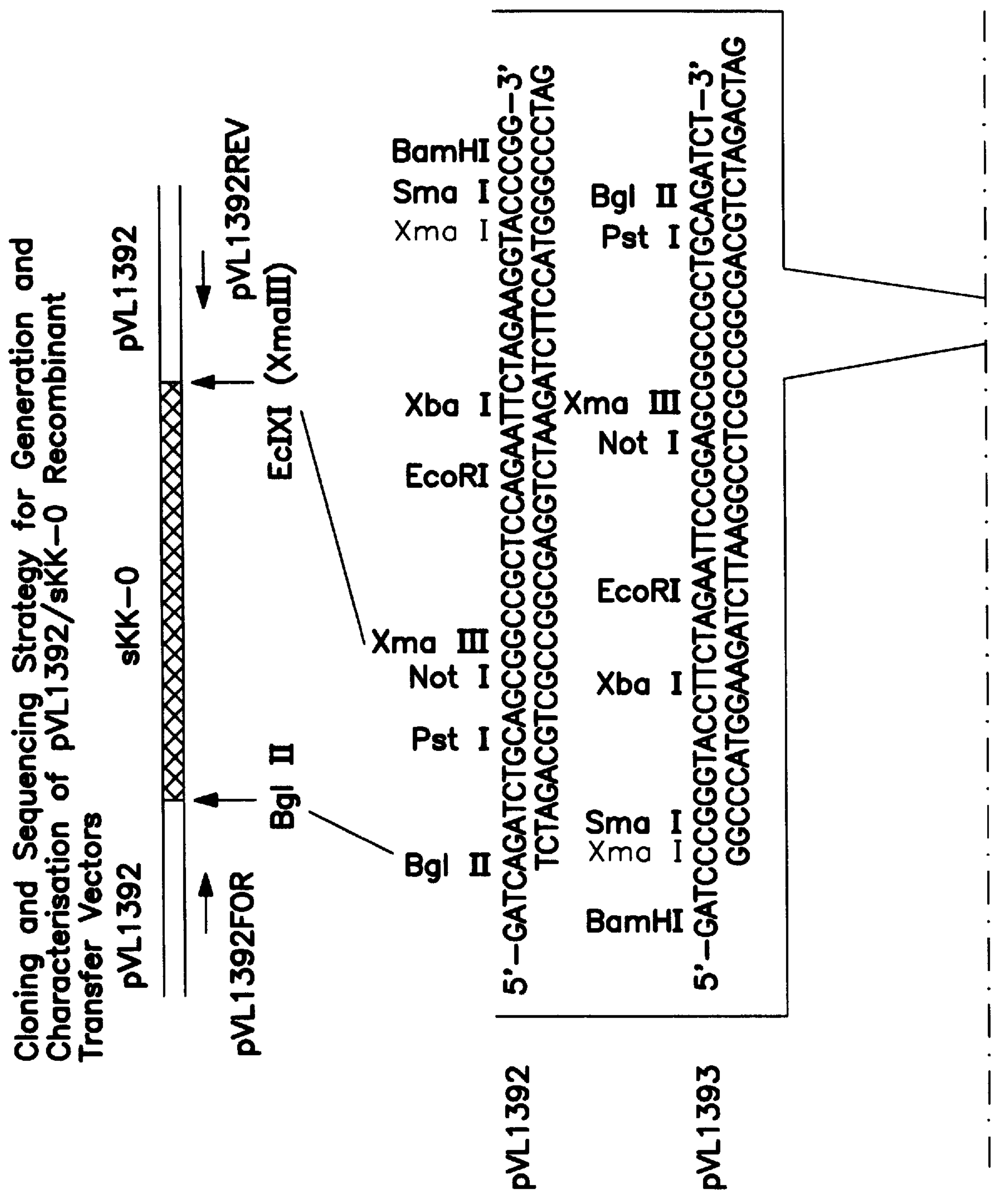
Figure 10B:
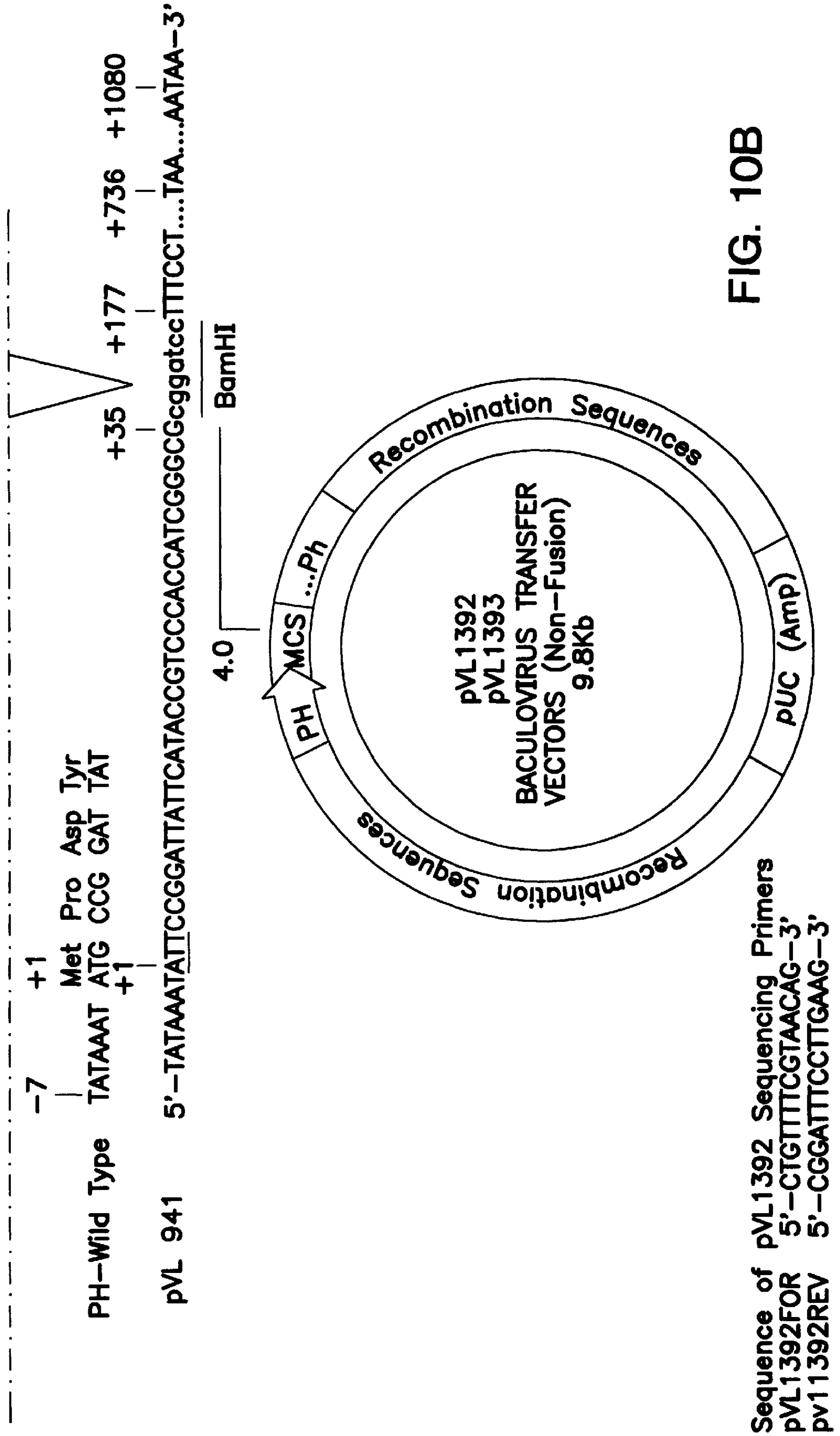

FIG. 5*a* shows a AcUW1 baculovirus which lacks the p10 gene;

FIG. 5*b* shows a complete AcUW1 baculovirus; i.e., a baculovirus having the p10 gene;

FIG. 5*c* shows a AcUW1 baculovirus having incomplete polyhedra and having lost virons;

FIG. 5*d* shows a complete AcUW1 baculovirus; i.e., a baculovirus having complete polyhedra and virons;

FIGS. 6*a* and 6*b* show the comparative structural features of the genomes of recombinant baculoviruses AcMNPV/pAcUW21/sKK-0 #1 and AcUW1-PH/sKK-0 #2;

FIG. 7 shows the sequence of a synthetic KK-0 (sKK-0) conotoxin gene showing the regions encoding pre-pro conotoxin KK-0;

FIG. 8 shows the sequence of a synthetic KK-0 conotoxin gene showing the location of restriction sites introduced to facilitate cloning and other manipulations;

FIG. 9 shows the sequence and relationships of oligonucleotides used for the assembly of a synthetic KK-0 conotoxin gene sKK-0;

FIG. 10 shows the cloning and sequencing strategy for the generation and characterisation of pVL1392/sKK-0 recombinant vectors;

FIG. 11 shows the sequence determined for the sKK-0 insert regions of transfer vector pVL1392/sKK-0 #2.2; and FIG. 12 shows comparisons of the predicted amino acid sequences of the precursors of *Conus textile* KK-0, KK-1 and KK-2 peptides and the predicted sequences of the corresponding mature peptides.

Figure 1:
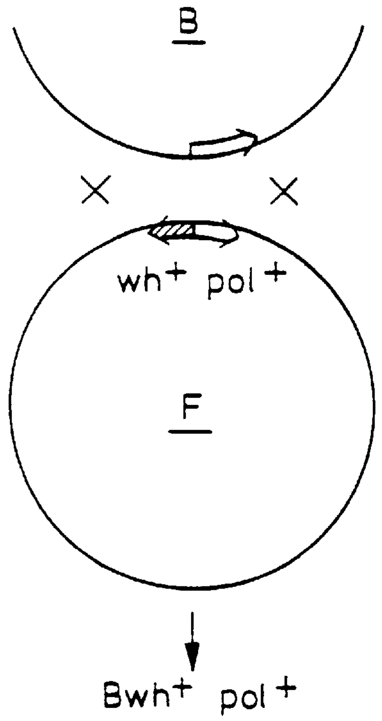
FIG. 1 shows a schematic representation of a recombination event involving a recombinant virus according to the prior art.

FIG. 1 shows a schematic representation of a recombination event involving a recombinant virus according to the prior art, wherein F is the prior art recombinant virus, B is the wild-type virus with which it is recombining, the crosses indicate regions of homology and hence define the region of co-transfer, $wh^+$ indicates the heterologous gene and $pol^+$ indicates the polyhedron gene.

In F, the $wh^+$ and $pol^+$ genes are in their conventional positions, i.e. the genes are extremely close together. There is very little sequence between the genes and therefore very little chance that it will be homologous to another virus, and hence able to act as a substrate for recombination. It will be appreciated that there is a very much greater chance of homologous sequences occuring either side of both genes, and thus a correspondingly much greater chance that both genes will move together as a unit during recombination.

Figure 2:
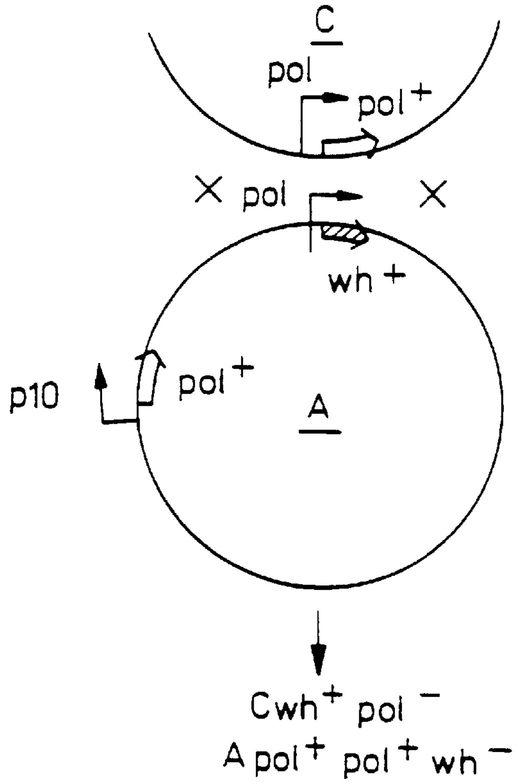
FIGS. 2, 3 and 4 show schematic representations of recombination events involving a recombinant virus according to the present invention.
Figure 3:
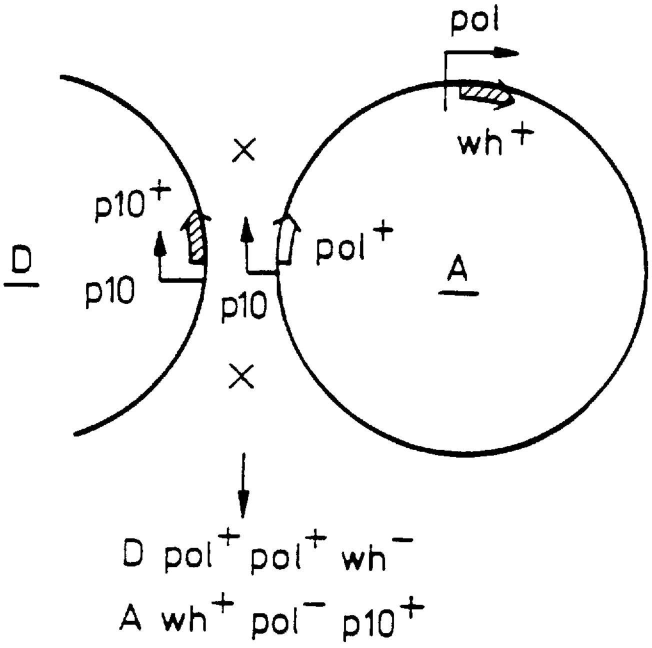

FIGS. 2 and 3 each show a schematic representation of a recombination event involving a recombinant virus according to one aspect of the present invention, represented by A, and a wild-type virus, C and D respectively.

It will be appreciated that the likelihood of co-transfer of both the $wh^+$ and $pol^+$ genes to another virus by homologous recombination is very much less with the recombinant of the present invention than with the prior art recombinant. The separation of the $wh^+$ and $pol^+$ genes in accordance with the present invention means that there is much more substrate between the genes upon which recombination events could occur, and therefore a correspondingly greater chance that both $wh^+$ and $pol^+$ genes will not be transferred together.

If recombination occurs around the position occupied by the $wh^+$ gene in A, as illustrated by FIG. 2, then the resulting A will have two $pol^+$ genes, but no warhead and the resulting C will have $wh^+$, but its lack of the $pol^+$ gene means that it will be crippled.

If recombination occurs around the position occupied by the $pol^+$ gene in A, as illustrated by FIG. 3, the resulting A will have $wh^+$, but will be crippled due to the lack of the $pol^+$ gene, and the resulting progeny virus D will not have the warhead.

Figure 4:
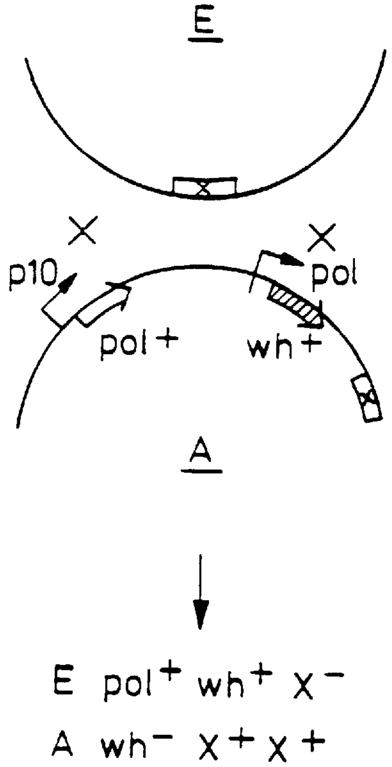

A further feature of the present invention is that even if $wh^+$ $pol^+$ are co-transferred, there is a greater likelihood than with the prior art that the virus to which they are transferred will lose at least one essential gene in the process, and thus be at least disabled or even non-viable. This situation is particularly true for co-transfer between distantly related viruses. This situation is shown schematically in FIG. 4, in which X represents the position of the essential gene. X is located in different positions on the genone in A and E, such that recombination as shown will result in loss of X from wild-type virus E.

Intrinsically a virus according to the present invention is:

safer than a construct based on more wild-type constructs;

safer with respect to likely recombination events; and straightforward to produce.

Preferably at least 10% of the genome of the baculovirus should separate the heterologous gene and polyhedrin gene. Even more preferably about 12% of the genome separates the two genes. This is illustrated for ease of reference only by FIGS. 6. In FIGS. 6 the location of sequences is reported with reference to the scale of 0–100 map units. AcMNPV has a genome of approximately 130/131 kilo base pairs in size. Therefore, according to the present invention the heterologous gene and the polyhedrin gene are preferably at least 13 kb , even more preferably about 15 kb to about 16 kb , apart.

Generally, the genomes of baculovirus range from about 90 to 200 kb. It will therefore be appreciated that the appropriate separation distance between the genes will depend on the baculovirus employed in the present invention.

Preferably, the polyhedrin gene is under the control of the p10 promoter, and the heterologous gene is under the control of any other promoter, for example the polyhedrin promoter.

Although this is a preferred embodiment, for the avoidance of doubt we would mention that the polyhedrin gene could be at any other position in the genome apart from its natural site, and where it did not disrupt an essential gene. The same is true of the heterologous gene.

It is also proposed that a recombinant which has a polyhedrin gene at the location normally occupied by the p10 gene, which p10 gene is disabled or deleted, and can be genetically manipulated to accommodate genes encoding insecticidal proteins at the position which would usually have been occupied by the polyhedrin gene provides a simple solution to the generation of diminished stability viruses. Such p10 deficient viruses have many features which render them both effective insecticides whilst still being genetically disabled with respect to wild-type viruses.

Thus, in accordance with another preferred embodiment of the present invention the genome has been modified to disable or delete the p10 gene.

Baculoviruses according to the present invention which also lack the p10 gene are also found to have the following features:

- insects which are infected with such a virus produce low yields of viral progeny at the time of death compared with insects infected at the same developmental stage with wild-type virus;
- the polyhedra produced are small and misshaped when compared to the wild-type polyhedra. They are thus likely to have reduced survival capacity;
- the polyhedra are however as infectious as wild-type polyhedra meaning that production will still be straightforward.

This feature of the invention is illustrated in FIGS. 5 (where Mag$^n$ =magnification). FIG. 5*a* shows a AcUW1 baculovirus which lacks the p10 gene. By comparison with the p10$^+$ AcUW1 baculovirus of FIG. 5*b*, it will readily be seen that the polyhedron of the p10$^-$ baculovirus is incomplete. A cluster of the disabled p10$^-$ AcUW1 baculoviruses is shown in FIG. 5*c*. This FIG. 5*c* illustrates that not only are the polyhedra incomplete, but that these baculoviruses have lost virons. Again the disabled baculoviruses in FIG. 5*c* can be compared with the healthier non-disabled baculoviruses shown in FIG. 5*d.*

In order to prepare these photographs polyhedra were fixed in 30% gluteraldehyde in 0.05M phosphate buffer for 90 minutes at 4° C., washed 3 times in buffer, and postfixed in 1% osmium tetroxide in 0.05M phosphate buffer. Following dehydration and infiltration the samples were embedded in Spurr's resin (Spurr, 1969), sectioned and stained in 2% alcoholic uranyl acetate for 15 minutes followed by 0.2% lead citrate in 0.1N sodium hydroxide for 5 minutes.

A preferred embodiment of the present invention is illustrated in greater detail by FIG. 6*b*, whose construction is described in the Examples below. This Figure can be instructively compared with the features of the recombinant baculovirus illustrated in FIG. 6*a*. FIG. 6*a* illustrates the conventional location of the heterologous gene, namely in close proximity to the polyhedrin gene.

Various preferred features and embodiments of the present invention will now be described by in greater detail.

The present invention will be described for ease of reference in relation to the use of a conotoxin as the heterologous gene, in particular, the mollusc and crustacean active "King Kong" conotoxin (Hillyard et al. (1989) Biochemistry), later designated KK-0 [SEQ ID 16] (Woodward et al. (1990) EMBO J. 9 1015–1020), and two related peptides KK-1 [SEQ ID 17] and KK-2 [SEQ ID 18] reported at the Conferences Jacques Monod on Toxines Animales (Aussois, France) on 24–28 Oct. 1988. As detailed in Example 1 below, synthetic peptides corresponding to the reported sequences of KK-0, KK-1 and KK-2 (see FIG. 12) were prepared and assessed by injection into specimens of adult *Periplanata americana* (Order: Dictyoptera) and larval *Heliothis virescens* and *Trichoplusia ni* (Order: Lepidoptera). Both the preparations KK-0 and KK-1 showed distinct insecticidal and/or paralysis inducing activity in each of the species tested. It will also be seen that use was made of a synthetic gene [SEQ ID 1] designed to encode an mRNA molecule which would in turn encode the presumed natural precursor of the "King Kong" (KK-0) conotoxin: a 78 amino acid protein which is likely to enter the secretion pathway during synthesis and may initially be produced as a pro-toxin which is subsequently processed to produce mature KK-0, at least in *Conus textile* (Woodward et al. (1990) EMBO J. 9 1015–1020). The synthetic gene we used for this work was designed without regard for the natural nucleotide sequence of the *Conus textile* KK-0 gene. Rather the gene was designed to ensure that, although it encoded the natural KK-0 precursor, it was likely to be both efficiently expressed in insect cell systems and was convenient to manipulate (see details in Example 2). Though we have not therefore used a natural KK-0 gene or cDNA from *Conus textile* there are, however, nG grounds to anticipate that such a sequence, or another synthetic gene capable of encoding the KK-0 precursor, would not be equally effective in enhancing the speed of action of a baculovirus host. The synthetic gene (sKK-0) we have employed actually has only 77% nucleotide sequence identity with the coding sequence of natural KK-0 mRNA. Further details of this toxin are given in our co-pending International Patent Publication No WO 94/23047.

It will be readily appreciated by a person skilled in the art that the present invention is applicable to other heterologous genes expressing insecticidal proteins, which are available or which are developed. Examples of such genes are genes expressing the toxin from the North African scorpion *Androctonus australis* Hector (AaIT), and genes expressing the Tox 34 toxin from the straw itch mite *Pyemotes tritici* (Tomalski MD and Miller LK, Nature, (1991), 352, 82–85).

The baculovirus may be *Autographa californica* Multiply Enveloped Nuclear Polyhedrosis Virus (AcMNPV) or any other available or developed viral species which is suitable for genetic engineering or manipulation techniques. Further examples include *Bombyx mori* NPV, *Spodoptera exigua* MNPV, *Galleria mellonella* MNPV, *Trichoplusia ni* MNPV, *Choristoneura fumiferana* MNPV, *Orgyia pseudotsugata* MNPV, *Spodootera frugiperda* MNPV, *Mamestra brassicae* MNPV, the so-called Celery Looper virus, designated HPV-85-CLMEV, mentioned in International Patent Publication No. W090/10387, the so-called NC-1 virus mentioned in our co-pending International Patent Application No. PCT/GB94/02438 and *Heliothis zea* SNPV (Single Enveloped Nuclear Polyhedrosis Virus).

Any pol$^-$ transmission vector suitable for use in connection with the modification of the baculovirus genome may be used in preparing the insect control agent of the present invention. Examples include pVL1392 and pVL1393. Other suitable vectors are known in the art.

A plasmid based on pVL1392 incorporating the DNA sequence of FIG. 7 and FIG. 8 has been introduced into *Escherichia coli* and deposited in the National Collection of Industrial and Marine Bacteria, Aberdeen UK, under the number NCIMB 40540, on 12 Mar. 1993.

A recombinant baculovirus according to the present invention can be constructed in accordance with known techniques. In general terms an appropriate transfer vector is constructed, as mentioned above. This transfer vector contains appropriate homologous sequences to the DNA sequences in the wild-type viral genome. Upon cotransfection of viral DNA and the plasmid vector, recombinant progeny are likely to arise due to homologous recombination. The recombinant viruses can then be separated from the parental viruses using conventional techniques.

Various preferred aspects of the invention will now be illustrated by means of the following Examples.

EXAMPLE 1

Biological Assessment of Synthetic Preparations of "King Kong" (KK-0), KK-1 and KK-2 Peptides Preliminary assessments of the biological activity of synthetic preparations of KK-0, KK-1 and KK-2 peptides were made in a series of injection studies using adult cockroaches (*Periplaneta americana:* Blattidae: Dictyoptera) and fifth-instar tobacco budworm larvae (*Heliothis virescens:* Noctuidae: Lepidoptera).

The proteins proved to be insoluble in distilled water and the standard aqueous buffers normally used for injection. KK-0 and KK-1 were suspended at a concentration of 10mg/ml in 0.1M ammonium bicarbonate. After gentle agitation for 1 hour the suspensions were filtered through a 0.2 μm filter. A visual assessment indicated that approximately 50% of the KK-0 product was solubilised whereas substantially less of the KK-1 product dissolved. This made it difficult to accurately quantify and compare dose rates directly for the different proteins. However, it was possible to estimate the maximum doses delivered. KK-2 was extremely hydrophobic and was dissolved in DMSO at a concentration of 10 mg of crude product per ml.

Tobacco budworm larvae (TBW) were injected using a 10 μl Hamilton syringe fitted with a 15 mm 33 gauge needle. Early fifth-instar larvae with an average body mass of approximately 300 mg were injected with 1–4 μl of each treatment. Typically, there were at least 5 replicates of each treatment. Adult male cockroaches were injected using a 50 μl Hamilton syringe fitted with a 15 mm 27 gauge needle. Each animal received a dose of 1–10 μl of test solution; average body mass was approximately 840 mg. Control insects were injected with an equivalent volume of the appropriate solvent.

After injection, treated insects were held individually in containers with a food supply under controlled conditions (25° C., 65% RH) for up to 72 hours. Observations were made periodically to check for any unusual symptomology.

Tobacco budworm

Injection of both KK-0 and KK-1 into *H.virescens* larvae resulted in a characteristic "flaccid paralysis" (Table I). Typically, symptoms were observed almost immediately after injection with larvae appearing to become "narcotised". Affected larvae were unable to stand and/or take a coordinated step. Furthermore, they were unable to reinvert when placed upon their back and were capable only of limited feeble movements of the mouthparts and claspers in response to stimulation (gentle prodding with a wooden cocktail stick). At the peak of the "narcosis", affected larvae were limp and pliable. These effects were relatively short-lived, however, and full recovery had normally occurred by 5–10 minutes after injection. All larvae were alive and well at 24 hours after treatment (24 HAT). Injection of higher doses led to an increase in both the severity and duration of the symptoms. The symptomology appeared to be more pronounced with KK-0.

No abnormal effects were observed following injection of KK-2 protein into *H.virescens* larvae at a single rate equivalent to a maximum dose of approximately 10 μg protein per larva (ie 33 μg protein/mg larva).

Cockroaches

All three proteins produced distinctive and debilitating effects in cockroaches (Table II). In each case, the severity of the effects increased with the volume of protein suspension injected.

Injection of KK-0 protein suspension into cockroaches initially caused severe tremoring followed by a loss of coordination, paralysis and knockdown. The effects were observed initially in the back legs but rapidly spread to the middle and finally the front legs leading to the collapse of the insect. Other symptoms included dorsal arching. Affected insects failed to recover and were dead by 22 HAT. Insects injected with the KK-1 protein showed similar symptomology although the effects appeared to be slightly less severe at the lowest dose of 1 μl of protein suspension.

Abnormal effects were also observed briefly in insects injected with 2 and 5 μl of the KK-2 peptide. Symptoms included arching of the back, flattening of the wings and loss of coordinated movement and occurred within a few minutes of injection. The effects appeared to be transitory and affected insects appeared to have fully recovered by 20 minutes post-injection. However, all animals in these treatments were dead at 72 HAT. No unusual symptoms were recorded in insects treated with the lowest rate (1 μl volume) and all insects were alive and well at 72 HAT.

These observations were confirmed in subsequent experiments and demonstrated that the conotoxin proteins have insecticidal activity against cockroaches and TBW larvae.

EXAMPLE 2

Synthetic King Kong (sKK-0) Conotoxin Gene Design

Since there was no a priori reason to believe that the codon usage of the natural KK-0 gene would be particularly advantageous for expression in insect cells, we decided to design a novel synthetic (sKK-0) gene. This was undertaken with the aid of such PCGene™ (Intelligenetics, 700 East Camino Real, Mountain View, Calif.) programmes as TRANSL, RESTRI and MUTSITE.

Features of the sKK-0 gene were that:

It encoded precisely the amino acid sequence [SEQ ID 2] for the KK-0 propeptide described by Woodward et al. through their cDNA cloning studies ((1990) EMBO J. 9 1015–1020).

The codons used to encode the KK-0 propeptide were selected because they are favoured or, at least, frequently encountered in insects (*Drosophila melanogaster*) and yeast (*Saccharomyces cerevisiae*) since it was anticipated that expression studies might also be undertaken in the latter organism (Ashburner et al. (1984) Develop. Genetics 4 295–312; Ikemura (1985) Mol.Biol.Evol. 2 13–34; Sharp (1986) Nucleic Acids Research 14 5125–5143).

The nucleotide sequence immediately preceding the translation initiation codon (ATG) matches closely the preferred sequence for animal mRNAs defined by Kozak ((Kozak (1981) Nucleic Acids Research 9 5233–5252; Kozak (1984) Nucleic Acids Research 12 857–873; Kozak (1986) Cell 44 283–292; Kozak (1987) J.Mol.Biol. 196 947–950).

No account at all was taken of the codons used by *Conus textile* to encode the KK-0 propeptide. (As a result the overall homology of sKK-0 and natural KK-0 genes is only 77.2%).

Flanking restriction enzyme recognition sites (upstream BglII and downstream XmaIII and BamHI) were incorporated into the design to facilitate direct cloning into the initially chosen baculovirus transfer vector pVL1392 (InVitrogen Corporation, 3985 Sorrento Valley Boulevard, San Diego, Calif.). Cloning with these enzymes was expected to result in the potential to transcribe the gene directly from the AcMNPV polyhedrin promoter carried by this transfer vector (see FIG. 10).

Several additional unique hexanucleotide recognition sequence sites were incorporated into the sKK-0 sequence at positions throughout the gene but without affecting the amino acid sequence encoded. These sites were included to facilitate recombinant characterisation and possible subsequent manipulations of the gene (see Example 14). None of the sites incorporated would result in the inclusion of particularly unfavourable codons.

The resultant sKK-0 sequence [SEQ ID 1] is shown in FIG. 7, highlighting the coding sequence for the KK-0 propeptide, and in FIG. 8, highlighting the position of restriction enzyme recognition sites.

EXAMPLE 3

Synthesis of an sKK-0 Gene

The strategy selected for assembly of the sKK-0 gene involved synthesis of overlapping complementary oligonucleotides encoding the DNA fragment shown in FIGS. 7 and 8 followed by DNA polymerase mediated completion of the single stranded regions and polymerase chain reaction (PCR) amplification to generate abundant quantities of the complete gene fragment (see FIG. 9).

Thus 4 oligonucleotides (ConoA, ConoB, ConoC, ConoD) [SEQ ID 3, 4, 5, 6], which together encode the complete sKK-0 DNA fragment, were synthesised by standard methods on an Applied Biosystems 380B DNA Synthesiser. Two additional shorter oligonucleotides, ConoPCR1 & ConoPCR2 [SEQ ID 7, 8], which are identical to the 5' 30 and 28 nucleotides of ConoA and ConoD were also synthesised to use as PCR primers. Each oligonucleotide was deprotected by incubation for approx. 8 hours at 55° followed by drying down under vacuum. They were then dissolved in 200 μl TE buffer (10 mM Tris/HCl (pH 8.0), 1 mM EDTA), concentrations measured by UV spectroscopy (1 $OD_{260}$ unit/ml. equivalent to approximately 20 μg/ml) and diluted with TE to give approximately 10 μM stocks. These were stored at −20° C. until use. sKK-0 synthesis reactions then comprised:

1) Mixing 5 μl each of 10 μM ConoA and ConoB in a sterile 500 μl conical polypropylene microfuge tube together with 5 μl 10 mM dGTP, 10 mM dATP, 10 mM dCTP, 10 mM TTP and 5 μl 500 mM KCl, 10 mM Tris-HCl (pH 8.5), 15 mM $MgCl_2$ 0.1% gelatine, making up to 49 μl with water and adding 1 μl (5 units) Taq DNA polymerase (Perkin/Elmer Cetus) before overlaying with 2 drops of light paraffin oil (Sigma). The tube was then capped, placed in a Techne PHC-1 Programmable Dri-Block® and subject to the following temperature cycle:

| | |
|---|---|
| 1.1' | @ 94° C. |
| 1' | @ 55° C. |
| 4' | @ 73° C. |

5 times, followed by a final incubation period of 7'@73° C.

2) Mixing 5 μl each of 10 μM ConoC and ConoD and treating exactly as in (1) above.

3) Taking 0.5 μl reaction (1) products mixing with 0.5 μl reaction (2) products and 5 μl reaction (1) products mixed with reaction (2) products. To each mixture was then added 10 μl 10 μM ConoPCR1; 10 μl 10 μM ConoPCR2; 10 μl 500 mM KCl, 100 mM Tris-HCl (pH 8.5), 15 mM $MgCl_2$, 0.1% gelatine; 10 μl 10 mM dGTP, 10 mM dATP, 10 mM dCTP, 10 mM TTP, and then making up to 99 μl with water before adding 1 μl (5 units) Taq DNA polymerase (Perkin/Elmer Cetus) and finally overlaying with two drops of light paraffin oil. In parallel, control reactions were set up which lacked PCR primers, reaction 1 or reaction 2 products. The reactions were then subject to the following temperature cycle in the Techne Programmable Dri-Block®:

| | |
|---|---|
| 1.1' | @ 94° C. |
| 1' | @ 68° C. |
| 4' | @ 73° C. |

25 times, followed by a final incubation period of 7'@73° C.

Analytical agarose gel electrophoresis on 10 μl aliquots of reaction 3 products then confirmed that only in those reactions which had contained all necessary DNA fragments and oligonucleotides had an approx. 270 bp fragment been produced. The remainder of each DNA fragment was then worked up by phenol extraction with an equal volume of water saturated phenol (twice) and then an equal volume of water saturated n-butanol (twice) before recovery by ethanol precipitation.

EXAMPLE 4

Assembly of pVL1392/sKK-0 Recombinant Transfer Vectors

After recovery, each of the above PCR products was subject to digestion with BglII and EclXI (an isoschizomer of XmaIII) restriction enzymes according to the manufacturers recommendations. In parallel an approx. 5 μg aliquot of pVL1392, a commercially available baculovirus (AcMNPV) transfer vector (InVitrogen), was similarly treated. Restriction digests were then run on a preparative 0.8% agarose/Tris-acetate electrophoresis gel containing 0.5 μg/ml ethidium bromide. The PCR products and the linearised vector DNA fragments were excised from the gel under UV illumination. They were then recovered by centrifugation through siliconised glass wool and ethanol precipitation. Aliquots of the isolated insert and vector DNA fragments were then mixed, together with T4 ligase in the appropriate buffer conditions (Sambrook J., Fritsch E. F. & Maniatis T. (1989) "Molecular Cloning: A Laboratory Manual". Cold Spring Harbor Press.). The ligation mixtures were then used to transform competent DH5α cells by standard methods (Sambrook et al. ibid.). Progeny transformants were selected by overnight growth on L agar plates containing 100 μg/ml ampicillin.

Transformants were then screened for the presence of sequences complementary to the sKK-0 gene by colony hybridisation on HyBond-N (Amersham International) filters by standard procedures (Sambrook et al. ibid.). The hybridisation probe used was oligonucleotide ConoB, which had been 5' phosphorylated by treatment with $g^{32}$P-ATP (Amersham International) and T4 polynucleotide kinase (Northumbria Biologicals Ltd.). Plasmid DNA was prepared from six strongly hybridising colonies. Restriction analysis of these DNAs suggested that three were pVL1392 derivatives containing inserts with approximately the size and features expected for sKK-0.

The sequence of the inserts present in the selected pVL1392 recombinants (#2.2, #5.2 & #6.1) was then checked using a Sequenase™ (USB, Cleveland, Ohio) kit and two synthetic oligonucleotide primers (pVL1392FOR and pVL1392REV) [SEQ ID 13, 14] designed to hybridise to the regions of pVL1392 flanking the BglII and XmaIII recognition sites and to allow sequencing of any insert introduced between those sites (see FIG. 10). The sequence of the insert [SEQ ID 15] in one of the three recombinants (#2.2) matched precisely that expected for sKK-0 cloned in the expected manner (see FIG. 11). The other plasmids contained inserts with minor sequence variations (mutations).

Recombinant #2.2, a derivative of transfer vector pVL1392 containing gene sKK-0 under the transcriptional control of the AcMNPV polyhedrin promoter, was therefore selected for all subsequent studies. An *E.coli* DH5α culture carrying recombinant plasmid pVL1392/sKK-0 #2.2 has been deposited in the National Collection of Industrial and Marine Bacteria, Aberdeen, UK as deposit number NCIMB 40540.

EXAMPLE 5

Generation of Recombinant (Polyhedrin Minus) AcMNPV Carrying sKK-0

Using standard baculovirus techniques, as described for example in King & Possee (1992) "The Baculovirus Expression System: A Laboratory Guide" (Chapman & Hall), recombinant AcMNPV virus carrying sKK-0 under the transcriptional control of the polyhedrin promoter, but lacking a functional polyhedrin gene, were generated by co-transfection of Sf21 cells with approx. 200 ng. SauI (Boehringer, Mannheim) linearised AcMNPV.lacZ (Possee & Howard (1987) Nucleic Acids Research 15 10233–10248) and 1 $\mu$g pVL1392/sKK-0 #2.2 DNA. Selection of recombinant virus was initially based on the inability of recombinant lacZ- virus to metabolise X-gal (GIBCO/BRL, Grand Island, N.Y.) in plaques generated in Sf21 cell monolayer culture. Six such lacZ- virus ("CONO-A", "CONO-B", "CONO-C", "CONO-D", "CONO-D" and "CONO-E") were picked and replated on Sf21 cells to purify them to homogeneity and confirm their inability to synthesise βgalactosidase. A small scale (approx. 4 ml) culture of each purified virus was then prepared by seeding $1.5\times10^6$ Sf21 cells in 4 ml. TC100/7.5% foetal calf serum medium (both from GIBCO/BRL) in a 25 $cm^2$ tissue culture flask (Bibby, Stone, Staffs.)), incubation overnight at 28° C., addition of 50% of the virus recovered by picking a single purified plaque and continuing incubation at 28° C. for a further 6 days. Aliquots of each of these virus stocks were then taken for bioassay (see Example 6). Parallel aliquots were used to prepare small samples of viral DNA for physical analysis (King & Possee (1992) ibid.).

Diagnostic physical analyses undertaken with the prospective sKK-0/AcMNPV recombinants were:

a) PCR studies with sKK-0 and, in parallel, βgalactosidase gene specific primers.

b) Southern blot analysis on viral DNA treated with ClaI and BglII, fractionated by electrophoresis on a 1% agarose gel, transferred to HyBond-N filters and hybridised with an isolated, random-primed $\alpha^{32}$P-dCTP labelled, sKK-0 probe.

These studies confirmed that virus "CONO-C" contained an sKK-0 gene, with all the expected physical features, and lacked a βgalactosidase gene. The other prospective recombinant viruses lacked the sKK-0 gene.

EXAMPLE 6

Bioassay of Prospective AcMNPV/pVL1392/sKK-0 Recombinant Virus

The biological activity of putative AcMNPV/pVL1392/sKK-0 viruses was evaluated in a series of injection studies using late-stage *Heliothis virescens* larvae. Aliquots of purified non-occluded virus were injected into fourth- or fifth-instar *H.virescens* larvae using a 10 $\mu$l Hamilton syringe fitted with a 15 mm 33 gauge needle. Typically, at least 5 larvae were injected per treatment with a standard volume of 1 $\mu$l volume of virus suspension. Control insects were injected with an equivalent volume of AcMNPV/pVL1392/lacZ virus, ACMNPV wild type virus or sterile water. After injection, larvae were held individually on artificial diet and examined at 24-hour intervals thereafter for a further 7 days. On each assessment occasion the number of live and dead larvae were recorded. Surviving larvae were examined for any unusual symptomology and/or behavioural responses.

Initially, aliquots of the six putative AcMNPV/pVL1392/sKK-0 clones generated as described in Example 5 were tested. Only one, AcMNPV/pVL1392/sKK-0 CONO-C, exhibited any unusual effects. The biological observations confirmed the physical analyses described in Example 5 which indicated that only the CONO-C virus carried the sKK-0 gene with all the expected physical features. Further injection assays to characterise the biological properties of AcMNPV/pVL1392/sKK-0 CONO C were carried out using titred stocks of the virus.

Data comparing the biological efficacy of AcMNPV/pVL1392/sKK-0 CONO-C and AcMNPV/pVL1392/lacZ viruses against early fourth-instar *H.virescens* larvae are presented in Table III. At 72 hours after treatment (72 HAT), 4/11 larvae treated with the AcMNPV/pVL1392/sKK-0 CONO C showed either full or partial flaccid paralysis. Larvae classified as "fully paralysed" were moribund: unable to stand, reinvert or walk and capable only of very feeble movements of the mouthparts and claspers in response to stimulation. "Partially paralysed" larvae showed local paralysis of the mid and posterior regions of the body although the anterior region including the head and mouthparts could respond normally to stimulation. These larvae could reinvert when placed on their backs and were capable of limited locomotion although movements were slow and poorly coordinated. At 96 HAT, all larvae treated with the AcMNPV/pVL1392/sKK-0 CONO C virus were either dead or showing abnormal symptomology. In contrast, all larvae injected with the AcMNPV/pVL1392/lacZ control virus were alive and behaving normally at 96 HAT; 1/10 of these larvae had died at 120 HAT and 6/10 larvae were dead at 144 HAT. AcMNPV/pVL1392 derivatives carrying the lacZ gene have a slower speed of kill than the wild type virus. Typically, the wild type AcMNPV starts to cause significant mortality at 120 HAT and beyond. Thus it may be concluded that the AcMNPV/pVL1392/sKK-0 CONO C construct has a faster speed of action and hence an enhanced insecticidal effect than both the AcMNPV wild type and AcMNPV/pVL1392/lacZ control viruses.

EXAMPLE 7

Assembly of pAcUW21/sKK-0 Recombinant Transfer Vectors

With the objective of preparing polyhedrin$^+$ (occluded) recombinant AcMNPV/sKK-0 derivatives, which would be infectious per os and hence capable of realistic assessment for dose response effects and for evaluation for crop protective effects, we chose initially to employ the pAcUW21 transfer vector (AMS Biotechnology (UK) Ltd.). This transfer vector is a simple derivative (Possee R. D., personal communication) of the transfer vector pAcUW2b previously used successfully to prepare recombinant viruses capable of delivering an accelerated biological effect because of the expression of insect selective toxin genes under the control of the powerful late p10 promoter (Stewart et al. (1991) Nature 352 85–88; McCutchen et al. (1991) Biotechnology 9 848–852).

To release a suitable sKK-0 insert for introduction into pAcUW21 a 20 μg aliquot of the pVL1392/sKK-0 #2.2 plasmid DNA was subject to digestion with EcoRI and BglII restriction enzymes. In parallel, a 10 μg aliquot of pAcUW21 transfer vector DNA was similarly treated. The restriction digests were then run on a preparative 1% agarose/Tris-acetate electrophoresis gel containing 0.5 μg/ml ethidium bromide. The released sKK-0 insert (approx. 282 base pairs) and the linearised vector DNA were excised from the gel under UV illumination. They were then recovered by centrifugation through siliconised glass wool and ethanol precipitation.

Aliquots of the isolated sKK-0 insert and pAcUW21 vector DNA fragments were then mixed, together with T4 ligase, in the appropriate buffer conditions (Sambrook et al. (1989) in "Molecular Cloning: A Laboratory Manual" (Cold Spring Harbor Press)). The ligation mixtures were then used to transform competent DH5α cells by standard methods (Sambrook et al. ibid.). Progeny transformants were selected by overnight growth on L agar plates containing 100 μg/ml ampicillin. Plasmid DNA was prepared from six putative recombinant colonies. Restriction analysis of these DNAs suggested that all six were pAcUW21 derivatives containing inserts with the size and features expected for sKK-0.

The sequence of the inserts present in two of the above six recombinants (#A1 & #A2) was then checked using a Sequenase™ (USB, Cleveland, Ohio) kit and two synthetic oligonucleotide primers designed to hybridise to the sKK-0 insert. The sequence of the inserts of both clones matched precisely that expected for sKK-0 cloned in the intended manner.

Recombinant #A1, a derivative of transfer vector pAcUW21 containing gene sKK-0 under the transcriptional control of the AcMNPV p10 promoter, was therefore selected for subsequent studies. This recombinant transfer vector also possesses an intact AcMNPV polyhedrin gene under the control of the natural polyhedrin promoter.

EXAMPLE 8

Generation of a Recombinant (Polyhedrin Plus) AcMNPV Carrying a p10 Promoter/sKK-0 Gene Expression Unit Standard baculovirus techniques (King & Possee (1992) "The Baculovirus Expression System: A Laboratory Guide" (Chapman & Hall)) were used to generate polyhedrin$^+$ (occluded) AcMNPV derivatives carrying the sKK-0 gene under the transcriptional control of the p10 promoter. This was accomplished by co-transfection of Sf21 cells with 200 ng.SauI (Boehringer Mannheim) linearised AcMNPV.lacZ (Possee & Howard (1987) Nucleic Acids Research 15 10233–10248) and 1 μg pAcUW21/sKK-0 recombinant #A1 DNA. Candidate recombinant AcMNPV/sKK-0 viruses were then selected by plaque purification on Sf21 cell monolayers (King & Possee (1992) ibid.) screening initially for inability of viruses to metabolise X-gal (GIBCO/BRL, Grand Island, N.Y.) and the ability to produce polyhedra (viral occlusion bodies) as judged by microscopy. Six such lacZ- virus (AcMNPV/pAcUW21/sKK-0 #1, AcMNPV/pAcUW21/sKK-0 #2, AcMNPV/pAcUW21/sKK-0 #3, AcMNPV/pAcUW21/sKK-0 #44, AcMNPV/pAcUW21/sKK-0 #45 and AcMNPV/pAcUW21/sKK-0 #6) were picked. A second plaque assay was then performed with the above six clones on Sf21 cell monolayers to purify them to homogeneity and confirm their inability to synthesise βgalactosidase and their ability to produce polyhedra.

A small scale cultures of each purified virus was then prepared as described in Example 5. Aliquots of each of these virus stocks were then taken for bioassay (see Example 9). Parallel aliquots were used to prepare small samples of viral DNA for physical analysis.

Southern blot analyses were performed on the prospective AcMNPV/pAcUW121/sKK-0 viral DNAs. These DNAs were treated with: (a) HindIII and (b) EcoRI and BamHI, fractionated by electrophoresis on a 1% agarose gel, transferred to Hybond-N filters and hybridised with an isolated, random-primed $\alpha^{32}$P-dCTP labelled, sKK-0 probe.

These studies confirmed that viruses AcMNPV/pAcUW21/sKK-0 #1, AcMNPV/pAcUW121/sKK-0 #4 and AcMNPV/pAcUW21/sKK-0 #5 each contained an sKK-0 gene, with all the anticipated physical features, lacked a βgalactosidase gene and produced polyhedrin$^+$ virus particles. Virus AcMNPV/pAcUW21/sKK-0 #1 was selected for all subsequent studies.

EXAMPLE 9

Bioassay of Prospective AcMNPV/pAcUW21/sKK-0 Recombinant Virus

The biological properties of putative AcMNPV/pAcUW21/sKK-0 viruses were evaluated in a series of injection and oral dosing studies against *H.virescens*. Injection assays using purified non-occluded virus stocks were carried out using the method outlined in Example 6. Oral dosing tests with purified polyhedra were undertaken using a modified version of the droplet feeding method for neonate larvae developed by Hughes and Wood ((1981) J.Invertebr. Pathol. 37, 54). Preliminary injection studies on the six putative AcMNPV/pAcUW21/sKK-0 viruses generated as described in Example 8 indicated that only three clones (AcMNPV/pAcUW21/sKK-0 #1,#4 and #5) were carrying the sKK-0 gene. Some of the larvae treated with these viruses exhibited abnormal symptoms which initially appeared to be analagous to those observed in insects treated with the AcMNPV/pVL1392/sKK-0 CONO C virus. Subsequent studies on AcMNPV/pCUW21/sKK-0 #1, however, confirmed that these "abnormal" effects were generally poorly defined and not particularly debilitating and that AcMNPV/pAcUW21/sKK-0 #1 showed no noticeable advantage over the wild type AcMNPV in terms of speed of action or insecticidal effect. Oral dosing studies comparing the biological efficacy of AcMNPV/pAcUW21/sKK-0 #1 and the wild type AcMNPV confirmed these observations.

EXAMPLE 10

Preparation of AcUW1-PH DNA for the Generation of Recombinant AcMNPV

In light of the different behaviour of polyhedrin minus AcMNPV derivatives in which the sKK-0 gene is expressed from the polyhedrin promoter (Examples 4,5 & 6) as compared to polyhedrin plus AcMNPV derivatives in which the sKK-0 gene was expressed from the p10 promoter (Examples 7, 8 & 9), we decided to construct a polyhedrin plus derivative in which the sKK-0 gene was expressed from the polyhedrin promoter to establish if improved insecticidal efficacy could be achieved with the polyhedrin promoter/sKK-0 expression unit but not with the p10 promoter/sKK-0 expression unit.

The virus selected as a recipient for the polyhedrin promoter/sKK-0 expression unit was AcUW1-PH (see Weyer et al. (1990) J.Gen.Virol. 71 1525–1534 and FIG. 6). This virus carries a p10 promoter/polyhedrin gene expression unit at the locus occupied by the p10 gene in wild type AcMNPV and a polyhedrin promoter/lacZ indicator gene expression unit at the location normally occupied by the polyhedrin gene. It will therefore form plaques on an Sf21 cell monolayer which contain cells carrying AcMNPV occlusion bodies and which stain blue in the presence of X-Gal indicator (GIBCO/BRL, Grand Island, N.Y.). Replacement of the polyhedrin promoter/lacZ expression unit with the polyhedrin promoter/sKK-0 expression unit of the pVL1392/sKK-0 #2.2 recombinant transfer vector was therefore anticipated to be a convenient means of preparing a polyhedrin plus AcMNPV derivative carrying a polyhedrin promoter/sKK-0 gene expression unit.

A stock of AcUW1-PH virus of unknown titre was kindly provided by Dr R. D. Possee (NERC Institute of Virology and Environmental Microbiology, Mansfield Road, Oxford). Small scale amplification cultures of this virus were then prepared by seeding 3 lots of $1.5\times10^6$ Sf21 cells in 4 ml. TC100/10% foetal calf serum medium (both from GIBCO/BRL) in 25 $cm^2$ tissue culture flasks (Bibby, Stone, Staffs.), incubation overnight at 28° C., followed by addition of 50 $\mu$l, 5 $\mu$l and 5 $\mu$l of a 1/10 dilution aliquots of the stock virus to one flask each and continuing incubation at 28 ° C. for a further 6 days. These small scale amplifications were titered using the standard plaque assay technique (King & Possee (1992) "The Baculovirus Expression System: A Laboratory Guide" (Chapman & Hall)). All plaques obtained contained inclusion bodies and stained blue in the presence of X-Gal. The virus stock produced from the initial 50$\mu$l input culture had a titre of $2.3\times10^7$ pfu/ml and was used to produce larger, 200 ml. spinner stock culturess of AcUW1-PH, from which purified stocks of virus and subsequently viral DNA were prepared by standard methods (King & Possee (1992) ibid. & Possee & Howard (1987) Nucleic Acids Research 15 10233–10248). A stock of linearised AcUW1-PH DNA was then prepared by digestion of 3$\mu$g viral DNA with SauI (Boehringer Mannheim) according to the manufacturer's recommendations since this enzyme cleaves only within the βgalactosidase gene and, as with AcMNPV.lacZ, this was anticipated to be a procedure which would facilitate production and detection of recombinant AcMNPV progeny (King & Possee (1992) ibid.).

EXAMPLE 11

Generation of Recombinant (Polyhedrin Plus) AcMNPV Carrying a Polyhedrin Promoter/sKK-0 Gene Expression Unit Using standard baculovirus techniques (King & Possee (1992) ibid.), recombinant AcMNPV viruses carrying sKK-0 under the transcriptional control of the polyhedrin promoter, with an active polyhedrin gene, were then generated by using the SauI linearised AcUW1-PH virus DNA as a recipient for the polyhedrin promoter/sKK-0 expression module from pVL1392/sKK-0 #2.2. This was accomplished by co-transfection of Sf21 cells with 200 ng. SauI linearised AcUW1-PH DNA prepared as described in Example 10 and 1 $\mu$g pVL1392/sKK-0 #2.2 DNA. Using the plaque assay technique, where the viruses generate plaques in Sf21 cell monolayer culture, recombinant virus were selected by initially screening for viruses which lacked the ability to metabolise X-gal (GIBCO/BRL, Grand Island, N.Y.) but retained the ability to produce occlusion bodies (polyhedra). Six such lacZ- virus (AcUW1-PH/KK0 #1, AcUW1-PH/KK0 #2, AcUW1-PH/KK0 #3, AcUW1-PH/KK0 #4, AcUW1-PH/KK0 #5, AcUW1-PH/KK0 #6) were picked. A second plaque assay was then performed with each of the above six clones on Sf21 to purify them to homogeneity and confirm their inability to synthesise βgalactosidase and their ability to produce polyhedra. Small scale cultures of each purified virus were then prepared by the methods outlined in Example 5. Aliquots of each of these virus stocks were then taken for bioassay (see Example 12). In parallel aliquots of the small scale virus stocks were used to prepare small samples of viral DNA for physical analysis.

Southern blot analysis were performed on the prospective AcUW1-PH/pVL1392/sKK-0 viral DNAs. These DNAs were treated with BglII and BscI (an isoschizomer of ClaI), fractionated by electrophoresis on a 1.4% agarose gel, transferred to Hybond-N filters and hybridised with an isolated, random-primed $\alpha^{32}$P-dCTP labelled, sKK-0 probe. These studies confirmed that viruses AcUW1-PH/sKK-0 #2, AcUW1-PH/sKK-0 #4, AcUW1-PH/sKK-0 #5 and AcUW1-PH/sKK-0 #6 each contained an sKK-0 gene, with all the anticipated physical features, lacked a βgalactosidase gene and produced polyhedrin virus particles.

Virus AcUW1-PH/sKKO #2 was selected for subsequent studies.

EXAMPLE 12

Bioassay of Prospective AcUW1-PH/pVL1392/sKK-0 Recombinant Virus

The biological efficacy of putative AcUW1-PH/pVL1392/sKK-0 recombinant viruses was evaluated in a series of injection and oral dosing studies against *Heliothis virescens* larvae. Injection assays with purified non-occluded virus stocks were undertaken using the methods described in Example 6. Oral dosing studies with purified polyhedra were carried out using a modified version of the droplet feeding assay described in Example 9.

Preliminary injection studies comparing the biological activity of the six putative AcUW1-PH/pVL1392/sKK-0 viruses generated as described in Example 11 indicated that only viruses AcUW1-PH/sKK-0 #2, AcUW1-PH/sKK-0 #4, AcUW1-PH/sKK-0 #5 and AcUW1-PH/sKK-0 #6 might have an enhanced insecticidal effect compared to the wild type virus. AcUW1-PH/pVL1392/sKK-0 #2 was selected for scale-up and further characterisation.

Injection assay data indicated that larvae treated with the AcUW1-PH/pVL1392/sKK-0 #2 virus demonstrated abnormal symptomology from 72 HAT onwards (Table IV). By 96 HAT the majority of larvae were dead and the only survivor was paralysed. All larvae were dead by 144 HAT. In contrast, no abnormal effects were observed in larvae treated with wild type AcMNPV until 120 HAT when 50% of larvae were dead; 100% mortality was recorded for the wild type AcMNPV at 144 HAT.

A series of oral dosing studies was carried out to compare the biological efficacy of AcUW1-PH/pVL1392/sKK-0 and the wild type AcMNPV using purified polyhedra. In all cases, the AcUW1-PH/pVL1392/sKK-0 #2 was shown to have a significantly faster speed of kill than the wild type and hence an improved insecticidal effect. Larvae treated with the AcUW1-PH/pVL1392/sKK-0 virus started to show symptoms of paralysis and death from 72 HAT onwards (Table V). Probit analysis of the dose response data confirmed that the speed of kill of AcUW1-PH/pVL1392/sKK-0

#2 was significantly faster than that of the wild type AcM-NPV at 72 and 96 HAT but that by 120 HAT the wild type virus had caught up.

The baculovirus of the present invention may be applied to the insect or locus of the insect in accordance with the known, or developed, techniques of the art. Preferably, the baculovirus is formulated. Any of the known, or developed, formulation may be used as appropriate. The formulations should be optimised to maximise speed of kill, and preferably protect the baculovirus from u.v. radiation.

Baculoviruses may be applied by air (particularly against forest pests), by a boom type sprayer for agricultural crops, or by high pressure equipment primarily for fruit and vegetable crops. They are generally applied by spray rather than in dust or granule formulation, the wettable powders being a preferred means of application. Adjuvants, for example surface active agents such as spreaders, stickers and emulsifiers, sunlight screens, buffers and also gustatory stimulants, may be added.

The fact that homologous recombination has occurred in accordance with the present invention can be ascertained using conventional methods. In particular, the precise change in the viral genome can be investigated using, for example endonuclease restriction or sequencing. Any changes in host range can also be assessed using known bioassay methods. It is also possible to follow the genetic make-up of viruses using a genomic marker.

Initial investigations into genetic exchange between engineered viruses and other viruses, or even acquisition of host cell DNA should be held in the laboratory, in which a group of larvae is infected with both wild-type and recombinant virus. Additional larvae can be added as representatives of successive generations.

Further investigations can be made using contained field trials. In such trails, larvae are infected in the laboratory before being introduced into the field, where the virus population is monitored over time.

TABLE I

Preliminary assessment of the biological activity of synthetic preparations of KK-0, KK-1 AND KK-2 proteins by injection into *Heliothis virescens* larvae[1]

| Treatment | Dose per insect | Effects |
|---|---|---|
| KK-0 | 1 μl | Loss of coordination within 30 secs post-injection. All larvae showing flaccid paralysis within 2–4 mins of injection & unable to stand, reinvert or respond to stimulation; limp & pliable. Effects began to wear off after 4–6 minutes & most larvae appeared normal at 10 mins post-injection. All larvae alive & well at 24 HAT. |
| | 2 μl | Symptoms as above but more severe & prolonged. Gradual recovery with all larvae appearing normal at 45 mins after injection. All alive & well at 24 HAT. |
| KK-1 | 1 μl | Symptoms first observed within 30 secs of injection. Most larvae showing flaccid paralysis within 2–4 minutes: symptoms as for KK-0. Effects were short-lived & all larvae appeared normal at 6–10 mins post-injection. All larave alive & normal at 24 HAT. |
| KK-2 | 1 μl | No adverse effects observed even at 24 HAT. |
| Control[2] | — | No adverse effects observed during experiment. |

[1]Six fifth-instar larvae injected per treatment; average body mass: 300 mg
[2]Control: 2 μl 0.1M ammonium bicarbonate

TABLE II

Preliminary assessment of the biological activity of synthetic preparations of KK-0, KK-1 and KK-2 proteins against *Periplaneta americana*[1] by injection.

| Treatment | Dose per insect | Effects |
|---|---|---|
| KK-0 | 1 μl | Temporary paralysis of back legs observed within 1 min post-injection but effects had disappeared by 6 mins pi. Capable of responding normally to stimulation but locomotion slow & poorly coordinated from 20 min–3 h pi. Moribund by 21 HAT & dead at 22 HAT. |
| | 5 μl | Tremoring followed by paralysis of back legs within 30 secs pi. Knocked down with mid- & hind legs paralysed by 20 min pi but front legs still working normally. Complete paralysis within 1 HAT. No recovery - moribund at 21 HAT & dead at 22 HAT. |
| | 10 μl | Tremoring & loss of coordination initially in back legs but rapidly spreading to mid- & front legs followed by total paralysis. No recovery - moribund/dead at 22 HAT. |
| KK-1 | 1 μl | Tremors followed by loss of movement in hind legs within 15 sec pi; front legs still actively moving at 5 min pi. Moribund at 20 min pi. Other symptoms included back arching. Some recovery between 1.5–3 HAT. At 21 HAT, insects knocked down & unable to reinvert. No recovery by 52 HAT. |
| | 5 μl | Loss of coordination & paralysis in hind legs immediately after injection, rapidly spreading to mid- & front legs. Complete paralysis within 5 min pi. No recovery & insects dead at 21 HAT. |
| | 10 μl | Rapid loss of coordination followed by complete paralysis within 30 secs pi. Occasional tremors observed thereafter but insects remained knocked down for remainder of experiment. No recovery & all dead at 21 HAT. |
| KK-2 | 1 μl | No abnormal effects observed throughout experiment. |
| | 2 μl | Abnormal symptomology included arching back & poorly coordinated locomotion within 1 min pi. Some recovery observed from 20 min pi onwards but insects dead at 69 HAT. |
| | 5 μl | Temporary loss of coordination immediately after injection; other symptoms included dorsal arching. Insects appeared to have recovered by 1.5 HAT but were dead at 45 HAT. |
| Control[2] | — | No abnormal effects observed throughout experiment. |

[1]Adult male roaches with an average body mass of 840 mg
[2]Control: 10 μl 0.1M ammonium bicarbonate solution

TABLE III

Evaluation of the biological efficacy of AcMNPV/pVL1392/sKK-0 CONO C by injection into *Heliothis virescens* larvae[6]

| | Number dead (+ affected) | | | | | |
|---|---|---|---|---|---|---|
| Treatment[1] | 24 hr | 48 hr | 72 hr | 96 hr | 120 hr | 144 HR |
| AcMNPV/pVL1392/lacZ[1] | 0/10 | 0/10 | 0/10 | 0/10 | 1/10 | 6/10 |
| AcMNPV/pVL1392/sKK-0 Cono C[1] | 0/11 | 0/11 | 0/11 (+3FP[3], 1PP[4]) | 3/11 (+1FP, 3PP, 4AF[5]) | 5/11 (+5FP, 1PP) | 11/11 |
| Control[2] | 0/7 | 0/7 | 0/7 | 0/7 | 0/7 | 1/7 |

[1]Dose rate = $1.5 \times 10^4$ pfu/larva.
[2]Control = Sterile water.
[3]FP - Full flaccid paralysis: insect is moribund, cannot stand, walk or reinvert & is capable only of limited feeble movements of mouthparts and claspers in response to stimulation; limp & pliable.
[4]PP - Partial paralysis: mid/posterior part of body is partially paralysed; larva is still capable of some locomotory activity and can reinvert but movements are poorly coordinated.
[5]AF - Affected: larva responds slowly to stimulation but is unable/unwilling to walk or feed.
[6]Fourth-instar larvae; average body mass = 100 mg.

TABLE IV

Evaluation of the biological efficacy of AcUW1-PH/pVL1392/sKK-0 #2 and AcMNPV wild type viruses by injection into *Heliothis virescens* larvae[6].

| | Number of insects dead (+ affected) | | | | | | |
|---|---|---|---|---|---|---|---|
| Treatment[1] | 1 | 2 | 3 | 4 | 5 | 6 | 7 |
| AcMNPV wt | 0/6 | 0/6 | 0/6 | 0/6 | 3/6 | 6/6 | 6/6 |
| AcUW1-PH/pVL1392/KK0–2 | 0/6 | 0/6 | 0/6 (+1PP[4], 1AF[5]) | 5/6 (+1FP[3]) | 6/6 | 6/6 | 6/6 |
| AcUW1-PH/pVL1392/lacZ | 0/7 | 0/7 | 0/7 | 0/7 | 0/7 | 3/7 | 7/7 |

TABLE IV-continued

Evaluation of the biological efficacy of AcUW1-PH/pVL1392/sKK-0 #2 and AcMNPV wild type viruses by injection into *Heliothis virescens* larvae[6].

| | Number of insects dead (+ affected) | | | | | | |
|---|---|---|---|---|---|---|---|
| Treatment[1] | 1 | 2 | 3 | 4 | 5 | 6 | 7 |
| Control[2] | 0/5 | 0/5 | 0/5 | 0/5 | 0/5 | 0/5 | 0/5 |

[1]Dose = $\sim 1 \times 10^4$ pfu/larva
[2]Control: Sterile water
[3]FP - flaccid paralysis; moribund and cannot stand, reinvert, walk or respond normally to stimulation; only sign of life indicated by very feeble movements of mouthparts/claspers in response to stimulation.
[4]PP - partial paralysis; cannot reinvert or walk; mid- & posterior part of body is completely immobilised but anterior portion of body can still move & pro- and false-legs can still be withdrawn in response to stimulation.
[5]AF - affected; insect can stand, reinvert & respond normally to stimulation but is incapable of coordinated locomotion.
[6]Fifth-instar larvae, average body mass = 300 mg.

TABLE V

Evaluation of the biological efficacy of AcUW1-PH/pVL1392/sKK-0 #2 and AcMNPV wild type viruses against *H. virescens* larvae by oral dosing[1]

| | Dose | % kill (+ % affected[2]) | | | | |
|---|---|---|---|---|---|---|
| Treatment | (PIBs/ml) | 72 hr | 96 hr | 120 hr | 144 hr | 168 hr |
| AcMNPV WT | $1.0 \times 10^7$ | 3 | 33 | 67 | 70 | 70 |
| | $3.3 \times 10^6$ | 0 | 7 | 17 | 20 | 20 |
| | $1.1 \times 10^6$ | 0 | 13 | 20 | 20 | 20 |
| | $3.7 \times 10^5$ | 0 | 0 | 7 | 10 | 10 |
| | $1.2 \times 10^5$ | 0 | 0 | 3 | 3 | 3 |
| | $4.1 \times 10^4$ | 0 | 0 | 4 | 4 | 4 |
| AcUW1-PH pVL1392 | $1.0 \times 10^7$ | 7 | 37 (+30) | 67 | 73 | 73 |
| sKK-0 #2 | $3.3 \times 10^6$ | 3 | 17 (+10) | 31 | 31 | 34 |
| | $1.1 \times 10^6$ | 4 (4) | 18 (+7) | 32 | 32 | 32 |
| | $3.7 \times 10^5$ | 3 | 10 (+3) | 14 | 14 | 14 |
| | $1.2 \times 10^5$ | 7 (+3) | 10 | 13 (+3) | 17 (3) | 20 |
| | $4.1 \times 10^4$ | 3 | 3 | 3 | 3 | 3 |
| Control | — | 0 | 0 | 0 | 0 | 0 |

TABLE V-continued

Evaluation of the biological efficacy of AcUW1-PH/pVL1392/sKK-0 #2 and AcMNPV wild type viruses against *H. virescens* larvae by oral dosing[1]

| Time after | AcMNPV wild type | | AcUW1-PH/pVL1392/sKK-0 #2 | |
|---|---|---|---|---|
| treatment | $LC_{50}$[3] | 95% C.I. | $LC_{50}$ | 95% C.I. |
| 96 | — | — | $6.1 \times 10^6$ | $3.3 \times 10^6$–$1.7 \times 10^7$ |
| 120 | $7.6 \times 10^6$ | $4.4 \times 10^6$–$1.9 \times 10^7$ | $5.2 \times 10^6$ | $2.7 \times 10^6$–$1.6 \times 10^7$ |
| 144 | $6.6 \times 10^6$ | $3.9 \times 10^6$–$1.5 \times 10^7$ | $4.3 \times 10^6$ | $2.3 \times 10^6$–$1.2 \times 10^7$ |
| 168 | $6.6 \times 10^6$ | $3.9 \times 10^6$–$1.5 \times 10^6$ | $4.0 \times 10^6$ | $2.2 \times 10^6$–$1.0 \times 10^7$ |

[1]Neonate larvae dosed using a modified version of the droplet feeding assay (Hughes & Wood, 1981); 30 larvae/dose.
[2]( ) % paralysed larvae
[3]$LC_{50}$ values (PIBs/ml virus suspension) estimated using a standard logit dose response procedure (Ashton, 1972).

I claim:

1. A recombinant baculovirus having a genome which comprises a polyhedrin gene and a heterologous gene, which expresses an insecticidal protein, wherein the polyhedrin gene and the heterologous gene are not under the control of the same promoter and at least 10% of the genome of the baculovirus separates the polyhedrin gene and the heterologous gene such that viral progeny produced by a recombination event with wild-type baculovirus which are viable progeny produced by a recombination event with wild-type baculovirus which are viable do not retain expression of both the polyhedrin gene and the heterologous gene.

2. A recombinant baculovirus according to claim 1 wherein at least one region of the genome which is homologous to a region of the genome of the wild-type virus occurs between the polyhedrin gene and the heterologous gene.

3. A recombinant baculovirus according to claim 1 wherein the polyhedrin gene and heterologous gene are located between two regions of the genome which regions are homologous to regions of the genome of the wild-type virus, wherein the location lacks an essential gene which is present between the homologous regions in the wild-type virus.

4. A recombinant baculovirus according to claim 1 wherein the polyhedrin gene is under the control of the p10 promoter.

5. A recombinant baculovirus according to claim 1 wherein the heterologous gene is under the control of the polyhedrin promoter.

6. A recombinant baculovirus according to claim 1 wherein the genome has been modified to disable or delete the p10 gene.

7. A recombinant baculovirus according to claim 1 wherein the separation is about 12% of the genome.

8. A recombinant baculovirus according to claim 1 wherein the polyhedrin gene and the heterologous gene are separated by at least 13 kilo base pairs.

9. A recombinant baculovirus according to claim 8 wherein the separation is about 15 kilo base pairs.

10. A recombinant baculovirus according to claim 1 wherein the polyhedrin gene and the heterologous gene are located in the same relationship to each other as they are in the construct shown in FIG. 6*b*.

11. The recombinant baculovirus according to claim 10 which is shown in FIG. 6*b*.

12. A progeny baculovirus of a baculovirus recombinant according to claim 1.

13. A method of combating insect pests at a locus which comprises treating the pests or locus with a recombinant baculovirus according to claim 1.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 269 base pairs
( B ) TYPE: nucleic acid
( C ) STRANDEDNESS: single
( D ) TOPOLOGY: linear ( i i ) MOLECULE TYPE: DNA ( i x ) FEATURE:
( A ) NAME/KEY: CDS
( B ) LOCATION: 17..250

( x i ) SEQUENCE DESCRIPTION: SEQ ID NO:1:

```
TTAGATCTAA TTCACC ATG AAG CTG ACA TGT ATG ATG ATC GTG GCC GTG     49
                  Met Lys Leu Thr Cys Met Met Ile Val Ala Val
                   1               5                  10

CTG TTC CTG ACC GCC TGG ACC TTC GCC ACT GCA GAC GAT CCC CGC AAC   97
Leu Phe Leu Thr Ala Trp Thr Phe Ala Thr Ala Asp Asp Pro Arg Asn
            15                  20                  25

GGC CTG GGC AAC CTG TTC TCC AAC GCC CAC CAC GAA ATG AAG AAC CCC  145
Gly Leu Gly Asn Leu Phe Ser Asn Ala His His Glu Met Lys Asn Pro
        30                  35                  40

GAG GCA TCC AAG CTT AAC AAG CGC TGG TGT AAG CAG TCC GGA GAG ATG  193
Glu Ala Ser Lys Leu Asn Lys Arg Trp Cys Lys Gln Ser Gly Glu Met
    45                  50                  55

TGT AAC CTG CTG GAC CAG AAC TGT TGT GAC GGC TAC TGT ATC GTG CTG  241
Cys Asn Leu Leu Asp Gln Asn Cys Cys Asp Gly Tyr Cys Ile Val Leu
60                  65                  70                  75

GTG TGC ACC TAGTGACGGC CGGATCCTT                                 269
Val Cys Thr
```

( 2 ) INFORMATION FOR SEQ ID NO:2:

( i ) SEQUENCE CHARACTERISTICS:
( A ) LENGTH: 78 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Met Lys Leu Thr Cys Met Met Ile Val Ala Val Leu Phe Leu Thr Ala
1 5 10 15

Trp Thr Phe Ala Thr Ala Asp Asp Pro Arg Asn Gly Leu Gly Asn Leu
20 25 30

Phe Ser Asn Ala His His Glu Met Lys Asn Pro Glu Ala Ser Lys Leu
35 40 45

Asn Lys Arg Trp Cys Lys Gln Ser Gly Glu Met Cys Asn Leu Leu Asp
50 55 60

Gln Asn Cys Cys Asp Gly Tyr Cys Ile Val Leu Val Cys Thr
65 70 75

( 2 ) INFORMATION FOR SEQ ID NO:3:

( i ) SEQUENCE CHARACTERISTICS:
( A ) LENGTH: 84 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

TTAGATCTAA TTCACCATGA AGCTGACATG TATGATGATC GTGGCCGTGC TGTTCCTGAC 60

CGCCTGGACC TTCGCCACTG CAGA 84

( 2 ) INFORMATION FOR SEQ ID NO:4:

( i ) SEQUENCE CHARACTERISTICS:
( A ) LENGTH: 89 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

GGATGCCTCG GGGTTCTTCA TTTCGTGGTG GGCGTTGGAG AACAGGTTGC CCAGGCCGTT 60

GCGGGGATCG TCTGCAGTGG CGAAGGTCC 89

( 2 ) INFORMATION FOR SEQ ID NO:5:

( i ) SEQUENCE CHARACTERISTICS:
( A ) LENGTH: 89 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:5:

CACGAAATGA AGAACCCCGA GGCATCCAAG CTTAACAAGC GCTGGTGTAA GCAGTCCGGA 60

GAGATGTGTA ACCTGCTGGA CCAGAACTG 89

( 2 ) INFORMATION FOR SEQ ID NO:6:

( i ) SEQUENCE CHARACTERISTICS:
( A ) LENGTH: 73 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:6:

AAGGATCCGG CCGTCACTAG GTGCACACCA GCACGATACA GTAGCTACAG TAGCCGTCTG 60

-continued

GTCACTAGGT TAC 73

(2) INFORMATION FOR SEQ ID NO:7:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:7:

TTAGATCTAA TTCACCATGA AGCTGACATG 30

(2) INFORMATION FOR SEQ ID NO:8:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

AAGGATCCGG CCGTCACTAG GTGCAC 26

(2) INFORMATION FOR SEQ ID NO:9:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

GATCAGATCT GCAGCGGCCG CTCCAGAATT CTAGAAGGTA CCCGG 45

(2) INFORMATION FOR SEQ ID NO:10:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

GATCCCGGGT ACCTTCTAGA ATTCCGGAGC GGCCGCTGCA GATCT 45

(2) INFORMATION FOR SEQ ID NO:11:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

TATAAATATG CCGGATTAT 19

(2) INFORMATION FOR SEQ ID NO:12:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:12:

TATAAATATT CCGGATTATT CATACCGTCC CACCATCGGG CGCGGATCC 49

( 2 ) INFORMATION FOR SEQ ID NO:13:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:13:

CTGTTTTCGT AACAG 15

( 2 ) INFORMATION FOR SEQ ID NO:14:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:14:

CGGATTTCCT TGAAG 15

( 2 ) INFORMATION FOR SEQ ID NO:15:

( i ) SEQUENCE CHARACTERISTICS:
( A ) LENGTH: 282 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:15:

GGCGCGGATC AGATCTAATT CACCATGAAG CTGACATGTA TGATGATCGT GGCCGTGCTG 60

TTCCTGACCG CCTGGACCTT CGCCACTGCA GACGATCCCC GCAACGGCCT GGGCAACCTG 120

TTCTCCAACG CCCACCACGA AATGAAGAAC CCCGAGGCAT CCAAGCTTAA CAAGCGCTGG 180

TGTAAGCAGT CCGGAGAGAT GTGTAACCTG CTGGACCAGA ACTGTTGTGA CGGCTACTGT 240

ATCGTGCTGG TGTGCACCTA GTGACGGCCG CTCCAGAATT CT 282

( 2 ) INFORMATION FOR SEQ ID NO:16:

( i ) SEQUENCE CHARACTERISTICS:
( A ) LENGTH: 78 amino acids
( B ) TYPE: amino acid
( D ) TOPOLOGY: linear ( i i ) MOLECULE TYPE: peptide ( x i ) SEQUENCE DESCRIPTION: SEQ ID NO:16:

Met Lys Leu Thr Cys Met Met Ile Val Ala Val Leu Phe Leu Thr Ala
1 5 10 15

-continued

| | | | | | | | | | | | | | | | |
|---|---|---|---|---|---|---|---|---|---|---|---|---|---|---|---|
| Trp | Thr | Phe | Ala | Thr | Ala | Asp | Asp | Pro | Arg | Asn | Gly | Leu | Gly | Asn | Leu |
| | | | 20 | | | | | 25 | | | | | 30 | | |
| Phe | Ser | Asn | Ala | His | His | Glu | Met | Lys | Asn | Pro | Glu | Ala | Ser | Lys | Leu |
| | | 35 | | | | | 40 | | | | | 45 | | | |
| Asn | Lys | Arg | Trp | Cys | Lys | Gln | Ser | Gly | Glu | Met | Cys | Asn | Leu | Leu | Asp |
| | 50 | | | | | 55 | | | | | 60 | | | | |
| Gln | Asn | Cys | Cys | Asp | Gly | Tyr | Cys | Ile | Val | Leu | Val | Cys | Thr | | |
| 65 | | | | | 70 | | | | | 75 | | | | | |

( 2 ) INFORMATION FOR SEQ ID NO:17:

( i ) SEQUENCE CHARACTERISTICS:
( A ) LENGTH: 77 amino acids
( B ) TYPE: amino acid
( D ) TOPOLOGY: linear ( i i ) MOLECULE TYPE: peptide ( x i ) SEQUENCE DESCRIPTION: SEQ ID NO:17:

| | | | | | | | | | | | | | | | |
|---|---|---|---|---|---|---|---|---|---|---|---|---|---|---|---|
| Met | Lys | Leu | Thr | Cys | Met | Met | Ile | Val | Ala | Val | Leu | Phe | Leu | Thr | Ala |
| 1 | | | | 5 | | | | | 10 | | | | | 15 | |
| Trp | Thr | Phe | Ala | Thr | Ala | Asp | Asp | Ser | Ser | Asn | Gly | Leu | Glu | Asn | Leu |
| | | | 20 | | | | | 25 | | | | | 30 | | |
| Phe | Ser | Lys | Ala | His | His | Glu | Met | Lys | Asn | Pro | Glu | Ala | Ser | Lys | Leu |
| | | 35 | | | | | 40 | | | | | 45 | | | |
| Asn | Lys | Arg | Cys | Ile | Glu | Gln | Phe | Asp | Pro | Cys | Glu | Met | Ile | Arg | His |
| | 50 | | | | | 55 | | | | | 60 | | | | |
| Thr | Cys | Cys | Val | Gly | Val | Cys | Phe | Leu | Met | Ala | Cys | Ile | | | |
| 65 | | | | | 70 | | | | | 75 | | | | | |

( 2 ) INFORMATION FOR SEQ ID NO:18:

( i ) SEQUENCE CHARACTERISTICS:
( A ) LENGTH: 77 amino acids
( B ) TYPE: amino acid
( D ) TOPOLOGY: linear ( i i ) MOLECULE TYPE: peptide ( x i ) SEQUENCE DESCRIPTION: SEQ ID NO:18:

| | | | | | | | | | | | | | | | |
|---|---|---|---|---|---|---|---|---|---|---|---|---|---|---|---|
| Met | Lys | Leu | Thr | Cys | Met | Met | Ile | Val | Ala | Val | Leu | Phe | Leu | Thr | Ala |
| 1 | | | | 5 | | | | | 10 | | | | | 15 | |
| Trp | Thr | Phe | Val | Thr | Ala | Asp | Asp | Ser | Gly | Asn | Gly | Leu | Glu | Asn | Leu |
| | | | 20 | | | | | 25 | | | | | 30 | | |
| Phe | Ser | Lys | Ala | His | His | Glu | Met | Lys | Asn | Pro | Glu | Ala | Ser | Asn | Leu |
| | | 35 | | | | | 40 | | | | | 45 | | | |
| Asn | Lys | Arg | Cys | Ala | Pro | Phe | Leu | His | Pro | Cys | Thr | Phe | Phe | Phe | Pro |
| | 50 | | | | | 55 | | | | | 60 | | | | |
| Asn | Cys | Cys | Asn | Ser | Tyr | Cys | Val | Gln | Phe | Ile | Cys | Leu | | | |
| 65 | | | | | 70 | | | | | 75 | | | | | |